US007381411B2

(12) United States Patent
Bogoch et al.

(10) Patent No.: US 7,381,411 B2
(45) Date of Patent: Jun. 3, 2008

(54) AGLYCO PRODUCTS AND METHODS OF USE

(76) Inventors: Samuel Bogoch, 46 E. 91st St., New York, NY (US) 10028; Elenore S. Bogoch, 46 E. 91st St., New York, NY (US) 10028

( * ) Notice: Subject to any disclaimer, the term of this patent is extended or adjusted under 35 U.S.C. 154(b) by 434 days.

(21) Appl. No.: 10/642,587

(22) Filed: Aug. 19, 2003

(65) Prior Publication Data

US 2004/0077532 A1    Apr. 22, 2004

Related U.S. Application Data

(60) Division of application No. 09/817,144, filed on Mar. 27, 2001, now Pat. No. 6,638,505, which is a division of application No. 09/146,755, filed on Sep. 4, 1998, now Pat. No. 6,242,578, which is a continuation-in-part of application No. 08/198,139, filed on Feb. 17, 1994, now abandoned.

(51) Int. Cl.
| | |
|---|---|
| *A61K 39/395* | (2006.01) |
| *A61K 38/00* | (2006.01) |
| *A61K 39/00* | (2006.01) |
| *C07H 21/00* | (2006.01) |
| *G01N 33/53* | (2006.01) |

(52) U.S. Cl. .............................. 424/141.1; 424/138.1; 424/139.1; 424/155.1; 424/185.1; 435/7.1; 435/69.3; 435/975; 530/326; 530/327; 530/395; 536/23.5

(58) Field of Classification Search ...................... None
See application file for complete search history.

(56) References Cited

U.S. PATENT DOCUMENTS

| | | | | | |
|---|---|---|---|---|---|
| 4,041,146 | A | * | 8/1977 | Giaever ...................... | 436/525 |
| 4,298,590 | A | * | 11/1981 | Bogoch ...................... | 424/1.49 |
| 4,486,538 | A | * | 12/1984 | Bogoch .................... | 424/156.1 |
| 4,840,915 | A | * | 6/1989 | Bogoch ...................... | 436/530 |
| 5,280,113 | A | | 1/1994 | Rademacher et al. ...... | 536/55.2 |
| 5,679,352 | A | | 10/1997 | Chong et al. ............ | 424/256.1 |

FOREIGN PATENT DOCUMENTS

WO    WO 96/32106    10/1996

OTHER PUBLICATIONS

Liu et al. Disruption of the single tropomyosin gene in yeast results in the disappearance of actin cables from the cytoskeleton. Cell. Apr. 21, 1989;57(2):233-42.*
Mickle et al. Genotype-phenotype relationships in cystic fibrosis. Med Clin North Am. May 2000;84(3):597-607.*
Voet et al. Biochemistry. 1990. John Wiley & Sons, Inc. 126-129 and 228-234.*
Weston et al. Sequence of the short unique region, short repeats, and part of the long repeats of human cytomegalovirus. J Mol Biol. Nov. 20, 1986;192(2):177-208.*
Yan et al. Two-amino acid molecular switch in an epithelial morphogen that regulates binding to two distinct receptors. Science 290: 523-527, 2000.*
Bogoch et al. Malignin antibody returns to normal on successful treatment of breast cancer. Paper presented at the International Symposium on Cofactor Interactions and Cancer Prevention; Nice, France; March 17-19, 1993; in the section on Diagnostic Markers. Published in Cancer Detection and Prevention 1993; 17(1).*
Bogoch et al. Malignin antibody and early malignancy. Lancet. Apr. 20, 1991;337(8747):977.*
Database Medline on STN, National Library of Medicine, (Bethesda, MD, USA), No. 99097253, Keppler et al.: *Elongation of the N-acyl side chain of sialic acid in MDCK II cells inhibits influenza A virus infection*, abstract, Biochemical and Biophysical Research Communications, Dec. 18, 1998, vol. 253, No. 2.
Database Medline on STN, National Library of Medicine, (Bethesda, MD, USA), No. 89028479, Bogoch et al.: *In vitro production of the general transformation antibody related to survival in human cancer patients: antimalignin antibody*; Abstract, Cancer Detection and Prevention, 1988, vol. 12, Nos. 1-6, pp. 313-320.
Database Medline on STN, National Library of Medicine, (Bethesda, MD, USA), No. 79094183, Kornblith et al.: *Growth-inhibitory effects of diphenylhydantoin on human brain tumor cells in culture*; Abstract, Mar.-Apr. 1978, vol. 2, No. 2, p. 122-127.
Seal et al.: *Elevation of Serum Protein-Bound Carbohydrates and Haptoglobin in Schizophrenia*, Clinical Chemistry; Oct. 1966, vol. 12, No. 10, pp. 709-716.
Bogoch S., et al., "Aglyco Pathology of Viral Receptors in Dementias", Annals of the New York Academy of Sciences, 757:413-417 (1995).
Abrams, M.B., et al., "Early Detection and Monitoring of Cancer with the Anti-Malignin Antibody Test", Cancer Detection and Prevention, 18(1):65-78 (1994).
Kornblith P.L., et al., "Growth-inhibitory effect of diphenylhydantoin on murine astrocytomas", Medline, XP-002199627 (Abstract), 1979.

* cited by examiner

*Primary Examiner*—Elizabeth C. Kemmerer
*Assistant Examiner*—Gregory S. Emch
(74) *Attorney, Agent, or Firm*—Kenyon & Kenyon LLP

(57)    ABSTRACT

Glycoconjugates, therapeutic compositions containing the glycoconjugates and therapeutic methods of using the glycoconjugates are disclosed. In particular, peptide constituents of aglyco 10B, which are immunogenic epitopes responsible for recognition of antigens by the immune system are provided. These glycoconjugates are useful in prevention of influenza virus binding to cells, treatment of schizophrenia and diagnosing chronic viral disease associated with development of cancer.

7 Claims, 11 Drawing Sheets

LEGEND FOR FIGURE 2— INCREASE IN ANTIMALIGNIN WITH AGE IN HEALTHY NON-TUMOR INDIVIDUALS; AND THE EFFECT OF A HIGH FREQUENCY CANCER FAMILY HISTORY.

| | | D COMPARED TO ··O·· |
|---|---|---|
| —□— SCREEN: UNKNOWN FAMILY HISTORY | 732 | <.001 |
| —O— NORMAL HEALTHY CONTROLS | 1,972 | |
| —◆— SCREEN: +ve FAMILY HISTORY, ASYMPTOMATIC | 193 | <.001 |
| —◆— SCREEN: +ve FAMILY HISTORY, SYMPTOMATIC | 181 | <.001 |
| TOTAL N= | 3,078 | |

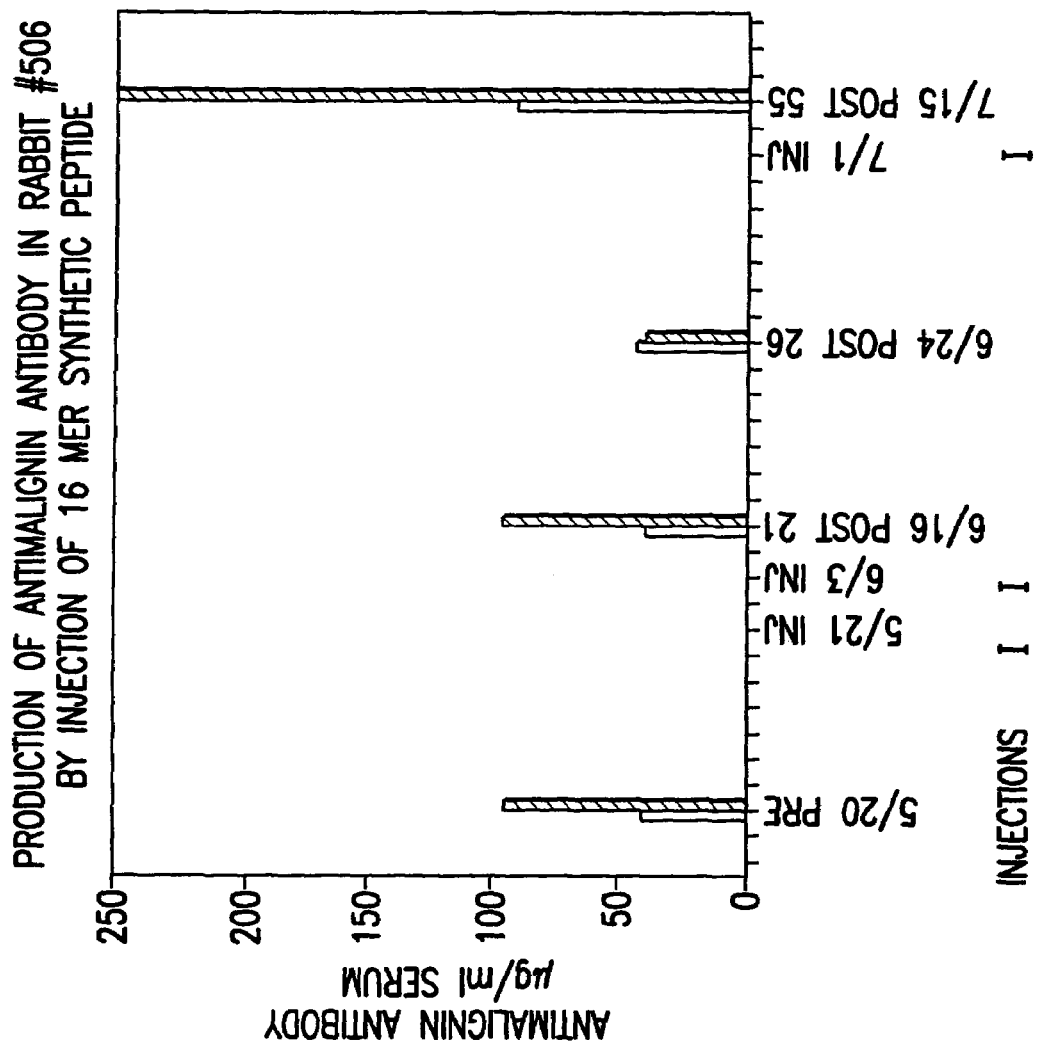

SEQUENCE LISTING

<160> NUMBER OF SEQ ID NOS: 2

<210> SEQ ID NO 1
<211> LENGTH: 16
<212> TYPE: PRT
<213> ORGANISM: Homo sapiens

<400> SEQUENCE: 1

Tyr Lys Ala Gly Val Ala Phe Leu His Lys Lys Asn Asp Ile Asp Glu
1               5                   10                  15

<210> SEQ ID NO 2
<211> LENGTH: 12
<212> TYPE: PRT
<213> ORGANISM: Homo sapiens

<400> SEQUENCE: 2

Gly Leu Ser Asp Gly Ser Asn Thr Glu Ser Asp Ile
1               5                   10

AGLYCO PRODUCTS AND METHODS OF USE

This application is a divisional application of patent application Ser. No. 09/817,144 (now Pat. No. 6,638,505 B2) filed Mar. 27, 2001, which is a divisional application of patent application Ser. No. 09/146,755 (now Pat. No. 6,242,578 B1) filed Sep. 4, 1998, which is a continuation-in-part of patent application Ser. No. 08/198,139 (abandoned) filed Feb. 17, 1994, which are incorporated herein in their entirety by reference thereto.

FIELD OF THE INVENTION

This invention concerns the discovery of products and methods to aid in the diagnosis and treatment of disorders of conjugated carbohydrate constituents of living organisms which contribute to cell dysfunction and cell death.

BACKGROUND OF THE INVENTION

Many seemingly unrelated observations made in the past, which were not understood and could not be understood, in terms of cell dysfunction, cell death and specific disease states can now be understood in the light of the methods and compositions of the present invention which defines for the first time the state of, and the consequences of, aglyco pathology, its products, as well as products and processes for its detection and treatment.

SUMMARY OF THE INVENTION

In one aspect of the invention there are provided peptides, in particular peptide constituents of aglyco 10B which are immunogenic epitopes responsible for the recognition of antigens by the body's immune system. In one embodiment of this aspect of the invention there are provided isolated glycoconjugates comprising at least one carbohydrate associated with the amino acid sequence set forth in SEQ ID NO.1 or SEQ ID NO.2. These peptide constituents of Aglyco 10B provide production in vivo of the specific antibody to Aglyco 10B, anti-Aglyco 10B (antimalignin antibody). In another embodiment of this aspect of the invention, the peptides, either individually or in combination, are included in a therapeutic composition for increasing the concentration of antimalignin antibody in patients in need thereof In another aspect of the invention there is provided, a method of preventing or inhibiting the attachment of influenza virus particles to a human patient's cells, comprising administering to the patient a therapeutically effective amount of a glycoconjugate to thereby bind to said influenza virus particles and prevent or inhibit attachment of the particles to cell receptors.

In yet another aspect of the invention there is provided a method of treating schizophrenia, comprising administering to a patient in need thereof a therapeutically effective amount of D-glucosamine-HCl to thereby increase the concentration of brain glycoconjugates in said patient.

In another aspect of the present invention there are provided monoclonal antibodies to the peptide having the amino acid sequence of SEQ ID NO.2 and monoclonal antibodies to aglyco protein 10B.

In another aspect of the invention, there is provided a method for diagnosing chronic viral disease associated with development of cancer in a patient, comprising detecting transformation to malignant cells by detecting abnormally elevated levels of antibody to aglyco protein 10B in the patient.

DESCRIPTION OF THE DRAWINGS

FIGS. 9A and 9B are bar graphs of the amount of anti-malignin antibody produced in vivo upon injection of rabbits with 16-mer synthetic peptide.

DETAILED DESCRIPTION OF THE INVENTION

Figure 1:
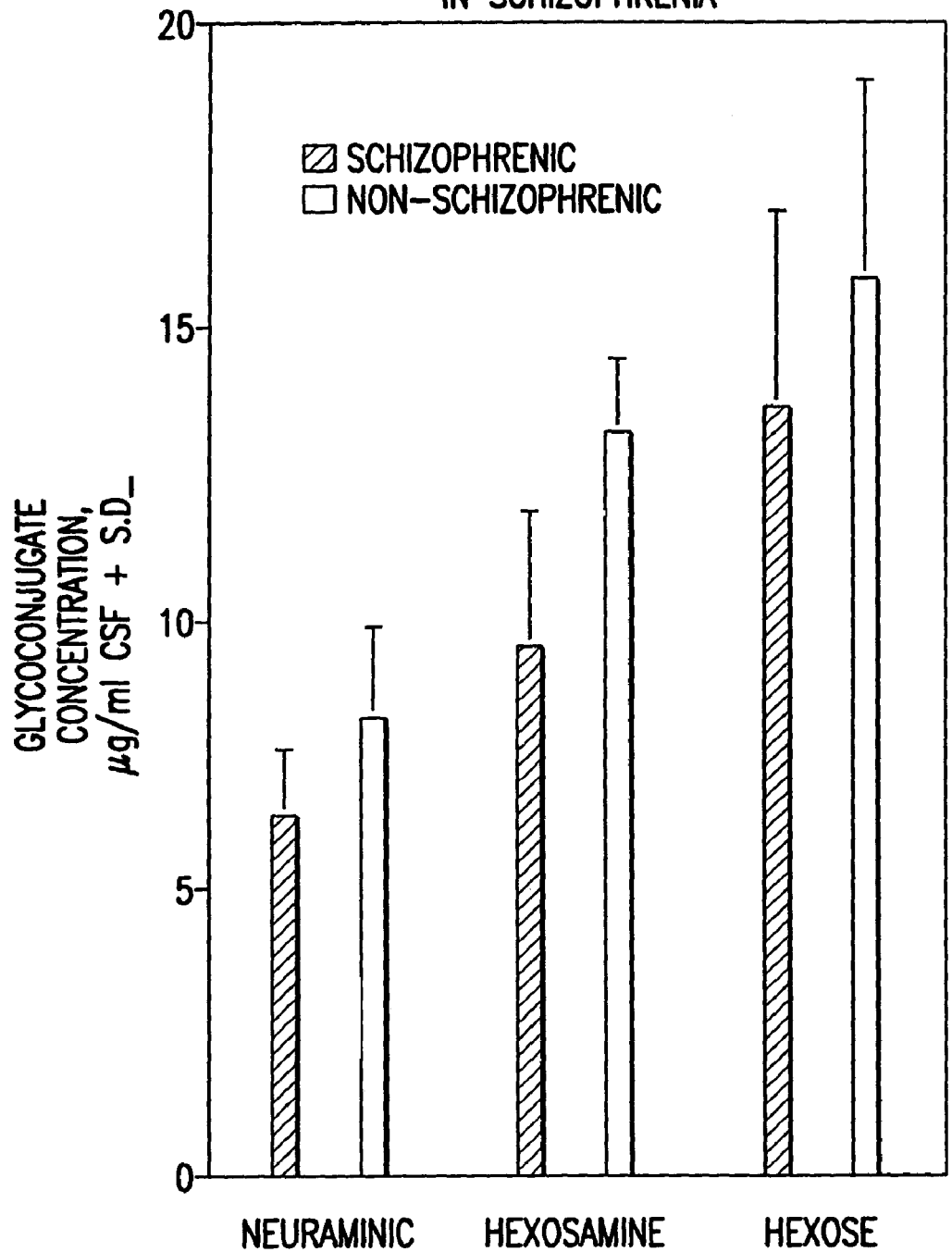
FIG. 1 is a bar graph showing the amounts of neuraminic acid, hexosamine and hexose in schizophrenic and non-schizophrenic patients.

The methods and compositions of the present invention have resulted from an investigation of aglycoconjugate pathology. It has been found by the present inventors that the carbohydrate constituents of glycoconjugates, which are covalently bound to lipid or protein to form the glycoconjugates, can contribute to cell stability, to receptor and recognition functions of the cell, and to the protection of cell constituents from damage by both native and foreign substances. When these normal carbohydrate constituents are reduced in concentration or otherwise structurally altered, together defined here as "aglyco states" and "aglyco pathology," the stability, receptor recognition and protective functions of these carbohydrates are diminished or lost, and cell dysfunction and cell death result, with resultant disease states depending on the location of the cell dysfunction or cell death. Evidence herein presented indicates that these disease states, in the nervous system for example, are a result of cell dysfunction or cell death (i.e., cell loss). Such disease states include, but are not limited to, the dementias such as schizophrenia (dementia praecox) and brain tumors, and also Parkinsonism and Alzheimer's disease.

Glycoprotein 10B is a normal 250 KD membrane constituent in human brain. This glycoconjugate has been shown to be involved in training in pigeon brain. It has been hypothesized that in brain glioblastoma, where apparent loss of contact inhibition of cell division is accompanied by unrestrained proliferation, the structure of 10B might be altered. Indeed, the structure of 10B is found to be markedly altered in brain glioblastoma: the carbohydrate groups are reduced in quantity by approximately 50% and there is a loss of heterogeneity. In normal 10B there are nine different carbohydrate constituents; in tumor 10B (aglyco 10B) these are reduced to five or six. Furthermore, the protein portion of 10B is overproduced or over expressed seven to ten fold. Astrocytin was the name given to the 10 KD peptide cleaved from brain tumor 10B. From glioblastoma cells grown in tissue culture, the equivalent to astrocytin, malignin, was isolated and it proved to be a very close structural relative of astrocytin. Malignin was so-named because in tissue culture the expression of this peptide, and thus its concentration per mg membrane protein extractable, increased with increased rate of cell division per unit time.

Recognin M, a 10 kD cancer polypeptide antigen rich in glutamic and aspartic acids, has been isolated from MCF7 malignant mammary cells. This polypeptide is related to malignin which has been isolated from glial brain tumors (Glu13, Asp9, His2). An IgM auto-antibody against Recognin M, antimalignin, has been isolated from human serum, produced as mouse monoclonal, produced in human form by challenge of human lymphocytes with the antigen in vitro, and has been isolated from malignant cells obtained at surgery and autopsy by elution and immunoabsorption to its immobilized purified antigen.

In a 20-year randomized, mostly-blind study involving several hundred physicians and three independent laboratories in the U.S., and three hospitals and one laboratory in the U.K., it was demonstrated that the concentration of antimalignin (anti-aglyco 10B) in serum, in µg/ml, (1) of normal healthy non-tumor-bearing humans increases moderately each decade between the third and the seventh, as the risk of cancer increases ($p<0.001$; N=1,972) (FIG. 1), (2) increases earlier and more markedly in as yet apparently unaffected members of high-risk cancer families ($p<0.001$; N=1,106) (FIGS. 1 and 2), and (3) is markedly increased in concentration in human serum within weeks of the occurrence of malignant transformation to clinical breast cancer, but is not stigmatic (in the sense of invariant) since it returns to normal within three months of successful treatment and remains in the normal range even up to 27 years after successful treatment (FIGS. 2 and 3) ($p.<0.001$; false positives and false negatives <5% on the first determination, <1% on repeat determination; N=600).

Figure 2:
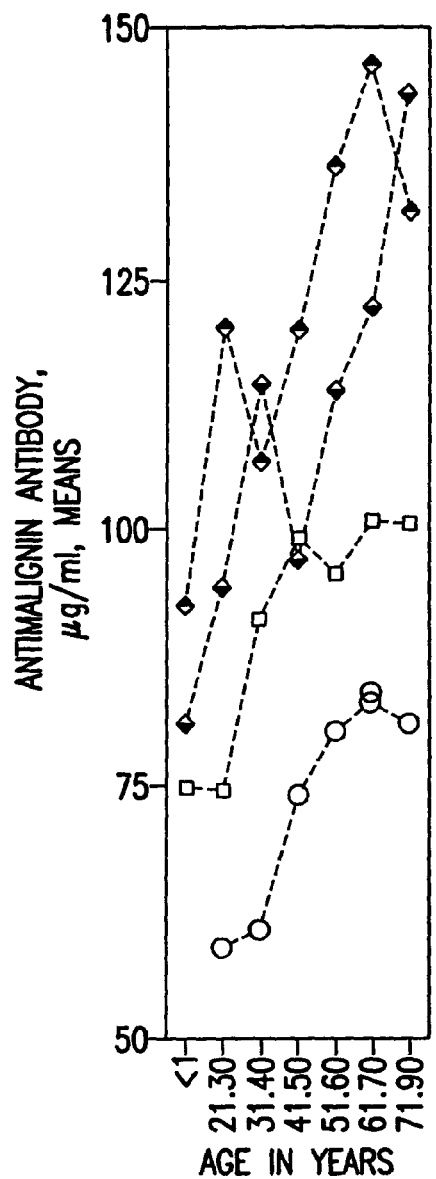
FIG. 2 is a graph of the amount of antimalignin antibody present with age in healthy individuals.
Figure 3:
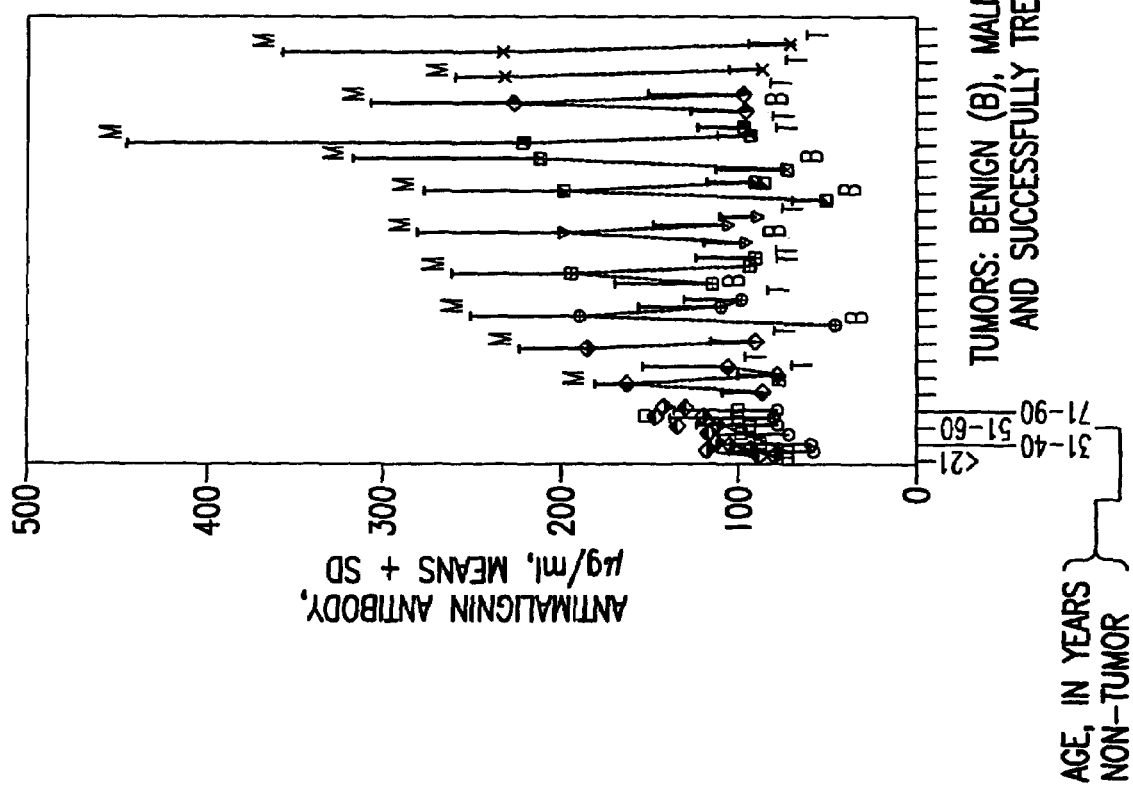
FIG. 3 is a plot of the amount of antimalignin antibody in healthy individuals and individuals presenting with various forms of cancer.

Readily biopsied cervix provided pathological evidence of transformation from dysplasia to the stage of frank invasive carcinoma. This was accompanied by marked elevation of the concentration of antimalignin. After surgical removal, antimalignin returned to normal within three months. FIGS. 2 and 3 show that these are statistically significant changes in both directions ($p<0.001$).

Quantitative determination of serum antimalignin antibody is therefore of interest for use as a non-invasive biomarker to indicate successful results in breast cancer chemoprevention trials.

In addition, purified antimalignin antibody, because of its demonstrated specificity in fluorescent and other chromogen staining of cell membranes in which the epitopes of malignin have become exposed, is applicable for use alone or as part of a battery of pre-dysplasia or dysplasia-based surrogate endpoint biomarkers in both individual and computerized cytometry.

Relation to Pathological Process

Antimalignin (Anti-aglyco10B) is an Inhibitory Transformation Antibody

Figure 4:
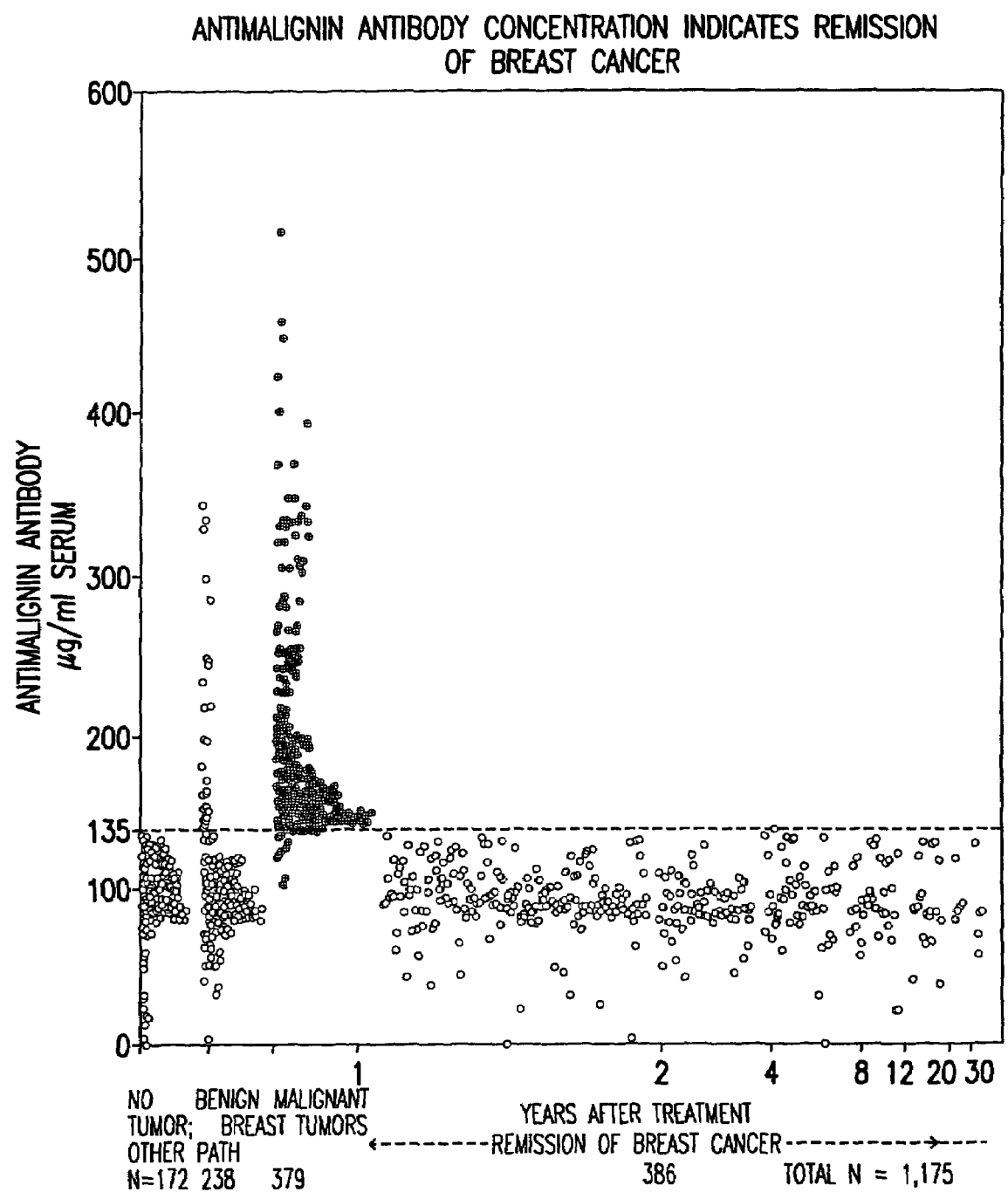
FIG. 4 is a plot of the amount of anti-malignin antibody observed in patients with breast cancer, during malignancy and years after treatment for the cancer.
Figure 5A:
FIG. 5 is a composition of photographs of immnostained malignant cells with anti-malignin antibody.
Figure 5B:
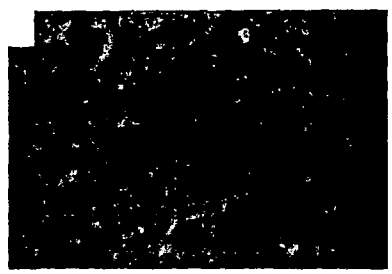
Figure 5C:
Figure 5D:
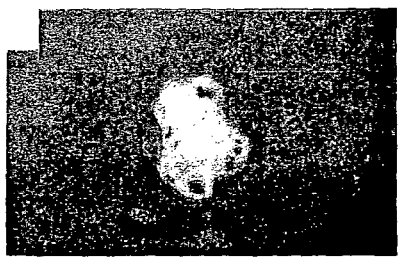
Figure 5E:
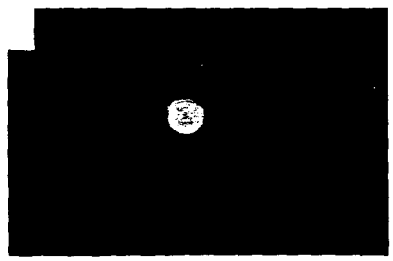
Figure 5F:
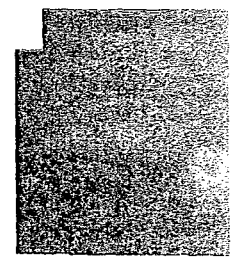
Figure 5G:
Figure 5H:
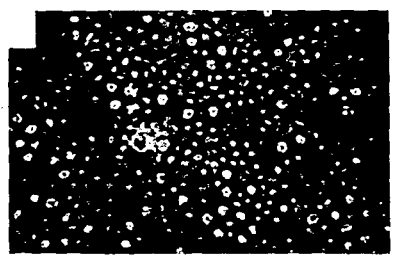
Figure 5I:
Figure 5J:
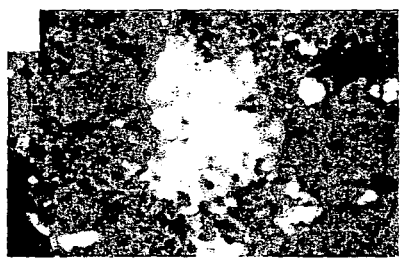
Figure 5K:
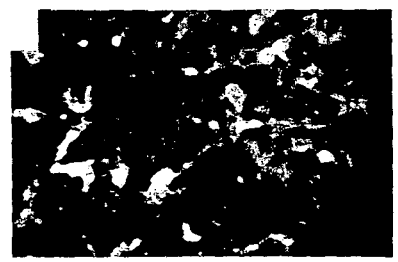
Figure 5L:

Cells which have undergone malignant transformation in humans may take years to, or may never, proliferate to become clinical cancer. If inhibition of proliferation is an immune process, as has been theorized and suggested by the increased incidence of cancer in immunodeficiency disorders such as AIDS, there is no direct evidence in human cancer of such an immune process, and the responsible mechanisms are unknown. Antimalignin, in addition to the properties listed above, has been shown to be quantitatively related to survival in patients. In vitro, antigen-purified human antimalignin binds to cancer cells regardless of cell type, is present in non-saturating amounts on cancer cells removed at surgery or autopsy, is cytotoxic to malignant glial cells (FIG. 4, k and l), and is inhibitory to the growth of small cell lung carcinoma cells at picograms of antibody per cell (FIG. 5).

The discovery of the role of glycoconjugates in the brain and the presence of specific antibodies to glycoprotein 10B in various disease states has led to the further discovery of specific aglyco 10B peptides and antibodies to these aglycopeptides that are associated with disease states. The above discovery of the role of glycoprotein 10B, aglyco pathology and antigenic aglyco peptides and the antibodies to these peptides has led to a totally unexpected finding of the relationship of certain chronic viral infections, viral safe havens, and viral carcinogenesis, and the discovery of new methods for the early detection and the treatment with a vaccine for chronic viral infections, such as AIDS and Hepatitis B or C. This work also has led to methods for detecting and treating various disorders that are affected by aglyco pathology.

In one aspect of the invention, neurological disorders may be diagnosed by the products of aglyco pathology as follows: 1) by direct determination of structural changes in the nervous system glycoconjugates, which changes produce novel aglyco products; or 2) because the novel aglyco products of this invention act as antigens, by determination of the novel antibody products produced by the body against the novel aglyco antigenic products. These aglyco cell antigen products are sufficiently different from the normal cell constituents that the body recognizes the new aglyco products as foreign and makes antibodies against them. These antibodies can have a deleterious or undesirable effect on the cell and cause cell death (e.g., in normal developing brain, which is not desirable; but in brain tumors, this result is desirable). The identification of these aglyco products by direct determination or by determination of antibodies raised against them is an aid to, or the basis for, diagnosis of the disorder as well as the basis for its treatment.

Glycoconjugate Receptors in Brain for Influenza Virus—'Glyco Decoys'

One function of glycoconjugates is to serve as receptors for the attachment of influenza virus to target cells in the brain. When the influenza virus approaches the cell, it attaches specifically to a glycoconjugate receptor located in the cell membrane. In the brain, a neuraminic acid-containing glycoconjugate serves as receptor. The neuraminic acid is cleaved from this receptor by means of a specific influenza virus enzyme, neuraminidase. In the case of one such receptor, the glycoconjugate of brain ganglioside, the cleavage of neuraminic acid brings the virus in contact with hexosamine which is a powerful inducer of the ejection of DNA from the virus, permitting its transfer into brain cells (Bogoch, et al., Virology, 7, 161-165, (1959).

In defense, cells which are targets of the virus release small molecular weight substances containing neuraminic (sialic) acid, the sialoresponsins (Bogoch,. et al., Nature, 195, 180 (1962), which are believed to act as decoys for the virus, thus preventing its attachment to and entry into the cells. The concentration of the sialoresponsins produced is related to the hemagglutination concentration of the virus.

The present methods and compositions employ this knowledge of the role of glycogonjugates in viral infections. Glycoconjugates or products which contain the neuraminic acid-hexosamine linkage, or any other glycoconjugate or structurally similar elements which are recognized by the virus as its receptor, are useful as preventive or therapeutic decoys in influenza and other virus or other infections which use this or similar configuration as receptor. Thus, in one aspect of the invention these aglyco decoys are administered per os, percutaneously, systemically (e.g., intravenously or intra peritoneally) or as spray for nasal or respiratory cavities or by any other means which can bring the virus and the decoy in contact with each other before the virus infects cells for the first time or infects additional cells after leaving the primary target cells. Thus, in this aspect of the invention there is provided a method for preventing or inhibiting influenza virus infection and the consequence loss of neuraminic acid.

Influenza Virus Infection, Brain Cell Loss and Deficient Neuraminic Acid and Hexosamine Aglyco Products in Schizophrenia The cell damage or cell death which results as a consequence of influenza virus infection in the developing brain is believed to cause or play a role in the cause of such neuronal disorders as schizophrenia.

Previous quantitative neurochemical studies suggested that neuraminic acid and hexosamine are part of a glycoconjugate intercellular recognition 'sign-post' system which forms the neural networks underlying normal brain development and behavior. Recent histological studies of schizophrenic brain reveal neuronal disorganization which has been suggested to result from a developmental injury. Epidemiological studies now suggest that infection prenatally with influenza virus, which contains neuraminidase, predisposes to schizophrenia. Furthermore, it has now been found that the concentration of conjugated neuraminic acid and hexosamine in cerebrospinal fluid is quantitatively decreased in schizophrenic patients.

The frequency of schizophrenia appears to be increased, from recent epidemiological observations, in individuals whose mothers had influenza virus infection during the second trimester of gestation (Callaghan, et al., Lancet, 337, 1248-1250 (1991)), and in populations with a high frequency of ganglioside and other glycolipid disorders (Rahav, et al., Am. J. Psychiatry, 143(10), 1249-1254 (1986)). Histological studies demonstrate neuronal cell loss and. neuronal disorganization in schizophrenic brain (F. E. Bloom, Arch. Gen. Psychiatry, 50, 224-227 (1993)). The removal of neuraminic acid from its conjugates by the influenza virus enzyme neuraminidase (sialidase) might be responsible for injury to neuronal cell recognition molecules in the immature brain. The above recent epidemiological and histological findings are relevant to quantitative neurochemical data which show a decease in the actual concentration of neuraminic acid and the hexosamine conjugates in cerebrospinal fluid (CSF) of schizophrenic patients (S. Bogoch, Am. J. Psychiatry, 114. 172, (1957)). Moreover, related work on glycoconjugate (glycolipid, glycoprotein) recognition substances in the brain (S. Bogoch, J. Am. Chem. Soc., 79, 3286, (1957)) led to the 'sign-post' hypothesis of neuronal connectivity and nervous system maturation (S. Bogoch, The Biochemistry of Memory; with an Inquiry into the Function of the Brain Mucoids. Oxford Univ. Press, 1968).

It previously has been demonstrated that glycoconjugates present in the nervous system are recognition substances (S. Bogoch, J. Am. Chem. Soc., 79, 3286, (1957); S. Bogoch, Biochem. J., 68, 319-324, (1958)). After the structure of the brain gangliosides was first determined, gangliosides were shown to act in vitro both as receptors for influenza virus and as effectors in stimulating clam heart and smooth muscle. In vivo, additional ganglioside administered intra cerebrally acts as a "decoy" and inhibits infection of brain neurones by influenza virus. Human brain glycoproteins have been isolated in bulk, separated and partially characterized in terms of their carbohydrate constituents. Glycoconjugates have been shown to be present in synaptic membranes and to be involved in mammalian neural development and in training and learning tasks in pigeons. The 'sign-post' function of glycoconjugates in the nervous system was postulated with reference to the establishment of neural networks, both during developmental maturation and with experience.

Schizophrenic patients have been shown to have a significant decrease of conjugated neuraminic acid and hexosamine in CSF compared to other psychotic disorders and normals (S. Bogoch, Nature, 184, 1628-1629 (1959)). This decrease is quantitatively proportional to the severity of the illness and increases toward normal with improvement in clinical status (Bogoch, et al., New Eng. J. Med., 264, 251-258 (1961)).

The present invention provides a beneficial treatment for schizophrenia and other medical conditions in which the concentration of aglyco protein is increased. In the present method for treating schizophrenia the concentration of glycoconjugates is increased and the amount of aglycoproteins in brain in the patient is decreased.

In the present method for treating schizophrenia, the neuraminic acid and hexosamine precursor, D-glucosamine-HCl, is administered to schizophrenic patients to improve the psychotic state of these patients. In particular, administration of about 50 to about 500 mg D-glucosamine HCl, preferably about 100 to 250 mg D-glucosamine HCl/day and most preferably about 200 mg D-glucosamine HCl/day improves the overall clinical health of schizophrenic patients by raising glycoprotein concentrations in the brain and lowering brain aglyco concentrations.

Aglyco Products in Alzheimer's Disease

Alzheimer's disease is a devastating wasting disease in which nerve cell loss is manifested by cognitive disturbances, predominately memory loss in early phases. Certain derivatives of the Amyloid Precursor Protein (APP) are responsible for the abnormal brain deposits characteristic of this disease. Although APP is known to be a glycoprotein, attention has not been focused on the carbohydrates in APP. Because of this invention, aglyco products can be detected (1) directly by isolation and characterization of the derivatives of APP in cerebrospinal fluid, which have decreased carbohydrate components, and/or (2) indirectly, by detection and quantification in patient's serum of antibodies to Aglyco APP.

Early pre-amyloid deposits in brain have been visualized before the neurofibrillary tangles, the products of nerve cell destruction, have appeared and joined the 'mature' Alzheimer plaque. These pre-amyloid deposits, like the mature plaques, contain Ab peptides, 3942 amino acid residues long degradation products of APP. While the transition from pre-amyloid to mature amyloid plaques is likely, since pre-amyloid deposits are present years before degenerating neurites appear in Down's syndrome patients' brain. Pre-amyloid deposits can be more amenable to treatment, that is, to dissolution and excretion before damage to nerve cells occurs. Protection against further accumulation of plaques can be afforded by administering dephenylhydantoin (DPH) which this invention demonstrates increases the concentration of protein-bound hexose in brain. DPH is administered intramuscularly, subcutaneously or intravenously to a patient in an amount in the range of about 0.5 to about 2 mg/kg body weight per day for as long as needed. The result is an increase in the amount of brain protein-bound hexose in the patient.

In another aspect of the invention, the carbohydrate constituents of brain glycoconjugates, which are reduced in concentration in the presence of brain tumors and other disease states, are increased toward normal concentration by administration of certain drugs, such as Diphenylhydantoin (DPH). Administration of DPH, in an amount in the range of from about 0.5 to 2 mg/kg body weight, preferably about 1 mg/kg body weight increases the concentration of brain protein-bound hexose, even in the absence of tumors. Thus, in this embodiment of the invention, there is provided a method for the treatment of brain or other malignancy which includes the administration of a therapeutically effective amount of DPH, which amount results in an increase in the level of glycoconjugates in the patient. An amount of about 1 mg/kg/day for days is sufficient to increase the concentration of brain glycoconjugates to normal or near normal levels. Treatment can be continued as long as necessary, preferably until the malignancy is reduced in size or completely gone.

Examples of other conditions in which new aglyco antigens may be exposed and give rise to aglyco antibodies are Parkinson's disease and multiple sclerosis, and the methods of the present invention should be applicable to these and other disorders, both of brain and other organs, both with regard to diagnosis and treatment as above.

Aglyco Antigenic Peptides and Antibodies to
Aglyco Peptides

Aglyco brain glycoprotein 10B and its specific antibody (monoclonal or polyclonal) are two aglyco products found in brain tumors and other malignancies. Aglyco 10B results from removal of carbohydrates from the normal glycoprotein 10B. The amino acid structures of aglyco 10B and several aglyco 10B fragments have been determined by several independent methods. The aglyco 10B peptide has been digested by several means into useful 12 mer and 16 mer peptide fragments, which have been shown to be antigenic. The antibody against aglyco 10B, which is of the IgM type, causes cell death.

The amino acid sequences of three peptide constituents of purified aglyco 10B were determined by iodobenzoic acid and trypsin hydrolysis, Edman degradation, autohydrolysis and microwave hydrolysis, and mass spectrometry. It was initially unknown whether these peptides, although clearly constituents of aglyco 10B, were actually immunologic epitopes (immunologically active antigen fragments). It has now been determined that the two longer sequences represent immunologic epitopes responsible for recognition by the body's immune system and the resultant production in vivo of the specific antibody, anti-aglyco 10B (antimalignin antibody). To establish this fact, the knowledge of the sequences of aglyco 10B has been used to synthesize in vitro synthetic peptides of the same sequence. These synthetic peptides have been injected into animals, and these animals produced the specific antimalignin antibody anti-aglyco 10B as tested by the standard immunoabsorption technique using immobilized intact aglyco 10B. Thus, aglyco 10B is the antigen, and these peptide fragments are indeed epitopes for both production of and binding of anti-aglyco 10B (antimalignin antibody). These synthetic peptides, when injected into an animal, induce the production of elevated concentrations of antimalignin antibody, thus establishing rigorously that the native biological aglyco substances are in fact responsible for the immune response discovered in human cancer. In addition, these synthetic peptides are useful as synthetic vaccines for increasing the body's own antimalignin antibody concentration. It previously has been established that antimalignin antibody concentration in serum is quantitatively related to length of survival in cancer patients, a synthetic anti-cancer vaccine has been produced.

The elevation in the absolute concentration of an antibody to aglycoprotein 10B (anti-aglyco 10B or antimalignin) is observed in many common malignancies of different cell types, such as cancer of the lung, breast, colon, etc. The elevations of the antibody illustrated that aglyco pathology is a general pathological phenomenon and not restricted to brain. Detection of an increase in the concentration of anti-aglyco 10B is a useful diagnosis of malignancy.

Aglyco Products and Processes are Used for the
Early Diagnosis and Treatment of Diseases Caused
by Viruses Which are Protected in Intracellular
Safe Havens Several viruses such as Hepatitis B and Hepatitis C, infection with which may lead to hepatocellular carcinoma, and HIV, which produces AIDS and an increase in the frequency of several malignancies, are resistant to both diagnosis and treatment by administration of anti-viral agents, in part, because the viruses become localized intra cellularly in a chronic latent state in what are known as intracellular safe havens. Thus, while there are a number of effective anti-viral agents such as the anti-proteases for HIV which can inactivate or destroy the HIV virus in extracellular fluids, they do not eradicate all of the virus in the body because some of the viruses are in cellular safe havens such as, for example, lymphocytes. Therefore, whereas a virus-free state of blood now may be achieved by treatment with anti-viral agents, when these treatments are stopped the viruses in the safe havens are often promptly released extracellularly and into the blood stream where they can infect new cells. Thus, these latent viruses may at any time reproduce and be released into extracellular fluids to infect other cells and eventually overcome the host.

In another example of the use of a safe haven by a virus, Hepatitis B or C may persist as a latent or chronic infection in the liver, lymphocytes, or other cells for many years and through established viral carcinogenesis, produce hepatocellular carcinoma. The cancers that result in relation to Hepatitis B or C carcinogenesis usually take years to reach the clinically detectable state, and there has been no way until the present invention to detect the malignant cells earlier and, therefore, to treat the cancer earlier.

It has now been discovered that these viral safe havens can be detected years earlier than previous detection methods allowed. Transformation of the infected cell to the malignant (immortal) state is a frequent, perhaps required process to establish and maintain the viral safe haven and, therefore, these safe havens can be destroyed (treated) even in the first few years after infection by means of administration of aglyco 10B or aglyco 10B synthetic antigen epitopes (vaccine) or anti aglyco 10B products (antibodies).

Carcinogenesis in the liver is an established consequence of Hepatitis B or C virus infection in humans (the virus is estimated to infect more than 1% of the population in the U.S. and 2% in Asia), but the detection of the presence of hepatocellular carcinoma (HCC) has been possible only late in the growth of the malignancy (usually only 10 to 25 years after the initial viral infection). This detection has been assisted by the levels of markers such as alpha fetoprotein, des-gamma-prothrombin and platelet-derived endothelial cell growth factor or the cancer becomes visible by scanning techniques (0.5-1 cm, representing billions of cells) all effective only late in the disease when other signs of malignancy are also clinically present.

The transformation to malignancy involves the immortalization of the cell so that it will live forever and not divide. This event creates a stable cell haven for the virus. The second stage of the progression of malignancy, increased cellular division (proliferation), has provided the only sign before the present invention to indicate that the first stage, transformation, has in fact occurred. Unfortunately by the time (10 to 25 years later) the stage of proliferation has produced clinically detectable cancer, for example, clinically apparent hepatocellular carcinoma, it is extremely difficult to treat the malignancy successfully.

In the present invention, a specific aglyco response which is present in the earliest stages of malignant transformation in hepatic malignancy permits earlier detection. Moreover, because of the nature of the aglyco change detected, the methods of the present invention provide a novel specific treatment for latent virus infection. It has now been discovered through detection of the elevation of specific aglyco products in the blood of a patient that the transformation of hepatic cells to the malignant state occurs decades earlier than previously thought—within the first few years after infection.

Diagnosis and Treatment of Viral Aglyco Disorders

The present invention provides an early detection and treatment regimen for hepato-cellular carcinoma and other carcinomas. In the diagnosis and treatment of viral aglyco disorders the following general procedures may be employed alone or in combination with other known methods of treatment or virus detection for the early treatment (before clinical cancer is apparent) of cells which have been transformed to the malignant state and for the destruction of intracellular safe havens for viruses infecting animals.

a) The diagnosis of a viral disorder, for example, Hepatitis B or C, or HIV, or other chronic viral infection, is made by well known standard procedures, for example, measuring the specific serum antibodies against the viruses' protein by established methods now in common use;

b) The presence of transformed (malignant, immortalized) cells may be demonstrated by determining the presence of elevated levels of antimalignin antibody in the serums according to the procedures described in the Examples, below;

c) Determination of the baseline (pretreatment) concentration of the virus in the blood of the patient (e.g., quantitative determination of specific viral RNA in serum, e.g. HIV-1 RNA assays) may be made;

d) Determination of the presence and concentration in blood and other body fluids of aglyco 10B or fragment peptides thereof, such as aglyco 10B "iodopeptide" and "trypsinpeptide" (see Examples) can be made;

e) One or more of the synthetic peptide vaccines according to the present invention is injected, preferably subcutaneously, in for example, about 50 to about 200 microgram amounts, preferably about 100 microgram amounts repeatedly, for example, but not limited to every 14 days, or other suitable time determined by the treating physician, until a maximum increase in antimalignin antibody is observed by quantitative determination in serum;

f) Antiviral chemotherapy (e.g. proteinase inhibitors, acyclovir) is administered by methods well established in the art to destroy or neutralize the virus, which has been released extracellularly from intracellular safe havens;

g) The concentration of the virus in the blood may again be determined (post treatment); according to Procedure c)(pretreatment).

h) The presence and concentration of aglyco 10B or fragment peptides thereof is determined according to procedure (d).

i) Procedures a) through h) may be repeated until the destruction of all transformed malignant cells is indicated, at about 90 to 120 days after the last injection of vaccine, by the return to normal levels of antimalignin antibody in serum (less than 135 µg/ml) according to procedure (b), by the absence of the further release of virus into the blood as determined according to procedure (c), and by the absence of aglyco 10B or fragment peptides thereof as shown by procedure (d), indicating that transformed malignant cells (containing aglyco antigenic products) are no longer present in the body.

j) The absence of cells transformed to malignancy at the end of the above treatment can be verified, and the degree of cellular proliferation of malignant cells visualized, quantitated, and monitored during the above treatment, by the administration intravenously of antimalignin antibody conjugated to $^{99}$Technetium or other suitable emitter and the recording with a gamma counter, for example over the liver in the case of Hepatitis B or C of the number and size of the malignant cell clusters in the liver smaller in size than those detected by non-specific scan techniques, and in HIV infection and AIDS, for example, over lymph nodes, spleen and brain.

k) Any persistent viral safe havens may be treated by antimalignin antibody or any other cancer chemotherapeutic agent which preferentially destroys malignant cells.

Similarly, the following is a procedure for the early treatment, destruction, or inactivation, before clinical cancer is apparent, or throughout the course of malignancy, of cells which have been transformed to the malignant state, where the transforming agent is other than a virus. Any combination of the following steps or partial steps may be employed. These steps and methods may be combined with other known methods of detecting and treating cancer.

a) The presence of transformed (malignant, immortalized) cells is determined by detection of elevated levels of antimalignin antibody in the serum;

b) The presence and concentration in blood and/or other body fluids of aglyco 10B or fragment peptides thereof are determined;

c) one or more of the synthetic peptide vaccines according to the present invention injected, preferably subcutaneously, in, for example about 50 to about 200 microgram amounts, preferably about 100 microgram amounts repeatedly, for example, but not limited to every 14 days, until a maximum increase in antimalignin antibody is observed by quantitative determination in serum;

d) The presence and concentration of aglyco 10B or fragment peptides thereof are determined according to procedure (b) and/or by determining the presence of elevated levels of antimalignin antibody in the serum;

e) Procedures a) through d) are repeated until the destruction of all transformed malignant cells is indicated at about 90 to about 120 days after the last injection of vaccine by the return to normal levels of antimalignin antibody in serum (less than 135 µg/ml) according to procedure b) and by the absence of aglyco 10B or fragment peptides thereof according to procedure (d) indicating that transformed malignant cells (bearing aglyco antigen products) are no longer present in the body;

f) The absence of cells transformed to malignancy at the end of the above treatment may be verified, and the degree of cellular proliferation of malignant cells visualized, quantitated, and monitored during the above treatment, by the administration intravenously of antimalignin antibody conjugated to $^{99}$Technetium or other suitable emitter and recording with a gamma camera;

g) Any persistent malignant cells are treated by antimalignin antibody or any other cancer chemotherapeutic agent which preferentially destroys malignant cells.

EXAMPLES

Example 1

We here illustrate a double-blind study which demonstrates the decrease in conjugated neuraminic acid and hexosamine in CSF of schizophrenic as compared to non-schizophrenic psychotic patients. Of 19 patients, two patients were excluded because the clinical diagnoses were not known. The remaining 17 patients were designated "schizophrenic" (N=11) if clinically appropriate, and "non-schizophrenic" other psychoses (N=6) when schizophrenia was not the diagnosis. These diagnoses were made by careful clinical work-up including full history and assessment of mental status with the Psychotic Characteristics Scale (Campbell, et al., Am. J. Psychiatry, 123, 952-962, (1967)) by research psychiatrists who had completed a minimum of three years of psychiatric residency training, and the diagnoses were confirmed by senior staff psychiatrists.

Lumbar CSF specimens of each of the 17 patients, 5 to 18 ml., coded, and without clinical information, were provided. Each of the specimens was lyophilized, dialyzed against distilled water exhaustively (cellophane pore size approx. MW 12,000 Daltons) at 0-5° C. to remove free neuraminic acid and free hexose, and the non-dialyzable fraction was quantitatively analyzed in duplicate for conjugated neuraminic acid by the Bial's orcinol and thiobarbituric acid (TBA) methods, conjugated hexosamine, and conjugated hexose, all as previously described (S. Bogoch, J. Biol. Chem., 235, 16-20 (1960)). After the neurochemical tests for all specimens were completed, the identification code for the patients was broken. Despite the small sample size, conjugated neuraminic acid (p<0.025) and conjugated hexosamine (p 0.006) but not conjugated hexose were statistically significantly lower in concentration in the schizophrenic group by two-tailed t test. Values of conjugated neuraminic acid in 81.8% of schizophrenics were less than 7.5 µg/ml CSF, and in 83.3% of non-schizophrenics were greater than 7.5 µg/ml CSF. Repetition of the test with three patients, one non-schizophrenic and two schizophrenic patients,. who had CSF drawn weeks apart, resulted in similar neurochemical analysis of the randomized blind specimens. However, determination of conjugated neuraminic acid by the TBA method was shown not to be reliable (Bogoch et al., Nature, 195, 180, (1962)). It should be emphasized that in the present and all previous studies, both in vitro and in vivo, it is only the conjugated, but not free, neuraminic acid which is found to be biologically active or creased in schizophrenia.

Thus, previous neurochemical data led to the normal 'sign-post' hypothesis, but the nature of the pathology of glycoconjugates was not understood until the present invention. The meaning of a decrease in the concentration of neuraminic acid and hexosamine, as glycoconjugates, has not previously been understood. That a decrease in these glycoconjugates pre- or post-natally, due to virus or other acute or chronic cause, is critical in the pathogenesis of schizophrenia has only now been realized. Consideration of the epidemiological evidence of the relation of influenza virus infection in the second trimester of pregnancy to frequency of schizophrenia, and histological evidence of brain cell loss and disorganization, taken together with direct evidence of the quantitative decrease in neuraminic acid and hexosamine concentration in glycoconjugates, has led to the present discovery of aglyco pathology.

Example 2

Administration of a neuraminic acid and hexosamine precursor to schizophrenic patients results in improvement.

D-glucosamine HCl, 200 mg per day, was administered per os to chronic hospitalized schizophrenic patients for 30 days. The Psychotic Characteristics rating scale was used, together with overall clinical observation to detect improvement or lack thereof. Over one half of the patients responded favorably and there were no untoward reactions.

Example 3

Increase in brain glycoconjugate hexose and in the incorporation of $^{14}$C glucose in pigeons during training.

The brains of pigeons at rest compared to training in a Skinner box were compared for (a) the absolute amount of glycoconjugate hexose and (b) the incorporation of $^{14}$C-glucose into brain glycoconjugates.

The results are as follows.

| (a) ABSOLUTE CONCENTRATION OF GLYCOCONJUGATE HEXOSE | | |
|---|---|---|
| | NUMBER of PIGEONS | GLYCOCONJUGATE HEXOSE MEAN mg/g WET WEIGHT BRAIN |
| RESTING - Never Trained | 21 | 0.63 |
| RESTING - 3 to 11 months post-training | 11 | 0.69 |
| TRAINING - 10 minutes | 1 | 9.0 |
| 20 minutes | 1 | 8.8 |
| 30 minutes | 5 | 10.0, 9.8, 3.9, 3.5, 2.7 |
| 45 minutes | 1 | 3.5 |
| 60 minutes | 5 | 7.8, 5.5, 2.4 |

(b) $^{14}$C-Glucose Incorporation into Pigeon Brain Glycoconjugates

Ninety microcuries of $^{14}$C glucose was injected intravenously into pigeons prior to a rest or training period, and the pigeons were sacrificed at intervals thereafter. The proteins of brain were then extracted and chromatographed from each pigeon brain and radioactivity determined on a scintillation counter. After exhaustive dialysis of the isolated brain protein groups, total radioactivity of the fraction was determined, then the fraction was subjected to stepwise acid hydrolysis with dialysis to free liberated sugars which were quantitatively determined. These sugar constituents were then separated by thin-layer chromatography, stained spots removed by vacuum suction and, together with blanks, counted.

| MINUTES after INJECTION | COUNTS/MINUTE TOTAL BRAIN GLYCOCONJUGATES | |
|---|---|---|
| | TRAINING | RESTING |
| 10 minutes | 2,000 | — |
| 20 minutes | 15,000 | — |
| 30 minutes | 21,000 | 1,000 |
| 45 minutes | 6,000 | 35,000 |
| 60 minutes | 1,500 | — |
| 120 minutes | — | 32,000 |
| 25.5 hours | — | 10,000 |

The time-course of incorporation is markedly different in the training state as compared to the resting state. In the training state, maximum incorporation occurs within 30 minutes at which time only 1/20 as much is incorporated in the resting state.

Example 4

Mice were divided into two groups, one half which were inoculated with subcutaneous brain ependymomas and one half which were not. Each of these two groups was divided into two groups. One half would receive daily subcutaneous DPH, 1 mg/kg body weight, and one half which received no DPH but saline injections only. Animals were sacrificed when the ependymoma grew sufficiently just to break the skin surface. There was a significant reduction in the growth of tumors when SPH was given. The brains were pooled for each subgroup, and extracted for protein-bound hexose as in Example 3, with the following results.

| TUMOR | BRAIN PROTEIN-BOUND HEXOSE AS % OF PROTEIN | |
|---|---|---|
| | WITHOUT DPH | WITH DPH |
| Absent | 4.6, 5.5 | 7.9, 8.0 |
| Present | 2.6, 2.3 | 6.8, 7.0 |

DPH produces an increase in the concentration of brain protein-bound hexose in the absence of tumors as well as in their presence.

Example 5

In Vitro Synthesis of Aglyco Products: 12 MER and 16 MER Synthetic Peptides

Two of the sequences of Aglyco 10B which we determined (Example 8), the 12 MER "Trypsinpeptide" GLSDGSNTESDI, and the 16 MER "Iodopeptide" YKAGVAFLHKKNDIDE, were synthesized in vitro. In Genosys peptide synthesis equipment, standard Fmoc chemistry was used on an Abacus system with high coupling efficiencies, in combination with TBTU activation of amino acids, with a non-swelling constant volume PEG polystyrene resin which helps maintain high concentrations of activated amino acids to drive each coupling reaction towards completion. The method of purification of the products used a C8 column (100% A) to (20% A:80% B). A=0.1% Trifluoroacetic acid (TFA) in distilled water. B=0.1 TFA in acetonitrile. All peaks were collected. Effluent was read at 220 nm. Criteria for purification were as follows: components of peaks were measured by mass spectrometry (on a Maldi-TOF by Perspective). HPLC (apparatus BioCad by Perspective Biosystems) was run to ensure >95% purity. Each peptide was analyzed by mass spectrometry and analytical HPLC to confirm the structure of the peptide, then submitted again to preparative HPLC, the desired peak isolated, and the final product analyzed again by reverse phase HPLC and mass spectrometry, providing the final purity of the peptide. The sequence of the synthetic peptide in each case, for the 12 MER peptide and the 16 MER peptide, were confirmed to be exactly the sequence determined by mass spectrometry of aglyco 10B, "trypsinpeptide" and "iodopeptide" respectively.

Example 6

The Synthetic Aglyco 12 MER and 16 MER Peptides Are Vaccines Which Produce Anti-Aglyco Products In Vivo and In Vitro Proof that the Peptide Sequences Determined in Aglyco 10B are True Epitopes for the Production of Antimalignin Antibody a) 12 MER Synthetic Peptide On day 1, after the baseline concentration of antimalignin antibody was determined in the serum of two not previously injected New Zealand white rabbits, #508 and #507, range 3 to 9 months in age, 100 micrograms of the 12 mer synthetic peptide GLSDGSNTESDI, synthesized in vitro and conjugated with adjuvant KLH (Keyhole Limpid Hemocyanin) and Freund's Adjuvant, were injected subcutaneously in each rabbit. Booster injections of the same peptide were made at day 14 and at day 42. the animals were bled from the auricular artery to determine antimalignin antibody concentration by the standard method as previously described, and shown in FIG. 6; that is, the antibody was immunoadsorbed against intact immobilized aglyco 10B (malignin) isolated from malignant glioblastoma cells grown in tissue culture. The antibody determinations on rabbit serum were performed at day 21, day 26 and day 55. Both (2/2) rabbits produced additional antimalignin antibody over the baseline uninjected serum levels.

Figure 7:
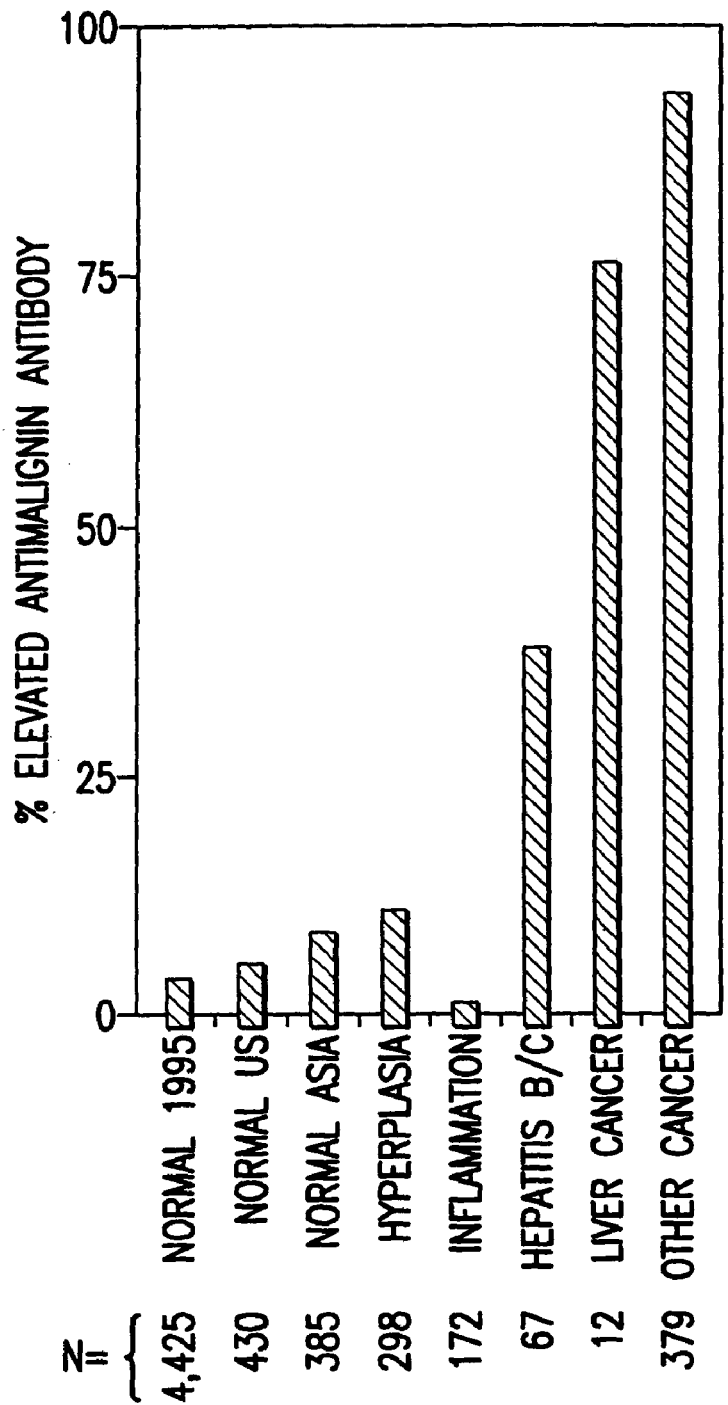
FIG. 7 is a bar graph of the amount of anti-malignin antibody concentration in benign hyperplasia, inflammation and cancer.

FIG. 7A shows the concentrations of antimalignin antibody at each bleed for rabbit #508, both the fast-binding antibody (F-TAG, open columns) and slow-binding antibody (S-TAG, solid columns). S-TAG concentration is seen to increase to a maximum of approximately seven-fold compared to the baseline level.

FIG. 7B shows the concentrations of antimalignin antibody at each bleed for rabbit #507, both the fast-binding antibody (F-TAG, open columns) and slow-binding antibody (S-TAG, solid columns). S-TAG concentration is seen to increase approximately threefold compared to the baseline level, and F-TAG concentration is seen to increase approximately fivefold compared to the baseline level. FIG. 7B also shows that the 26-day bleed in rabbit #507, and to a lesser extent in the 21-day bleed in rabbit #508, caught the fact that the increase in F-TAG preceded the maximum increase in S-TAG concentration. This increase in F-TAG before the increase in S-TAG is the same as that seen in vitro when isolated lymphocytes in tissue culture are induced by intact Aglyco 10B to produce antimalignin antibody (*Cancer Detection and Prevention* 12:313-320, 1988). The repetition of this phenomenon with synthetic peptide epitopes injected into rabbits is further confirmation of the fact that the synthetic peptides reproduce exactly the production and release into serum of antimalignin antibody.

Figure 6:
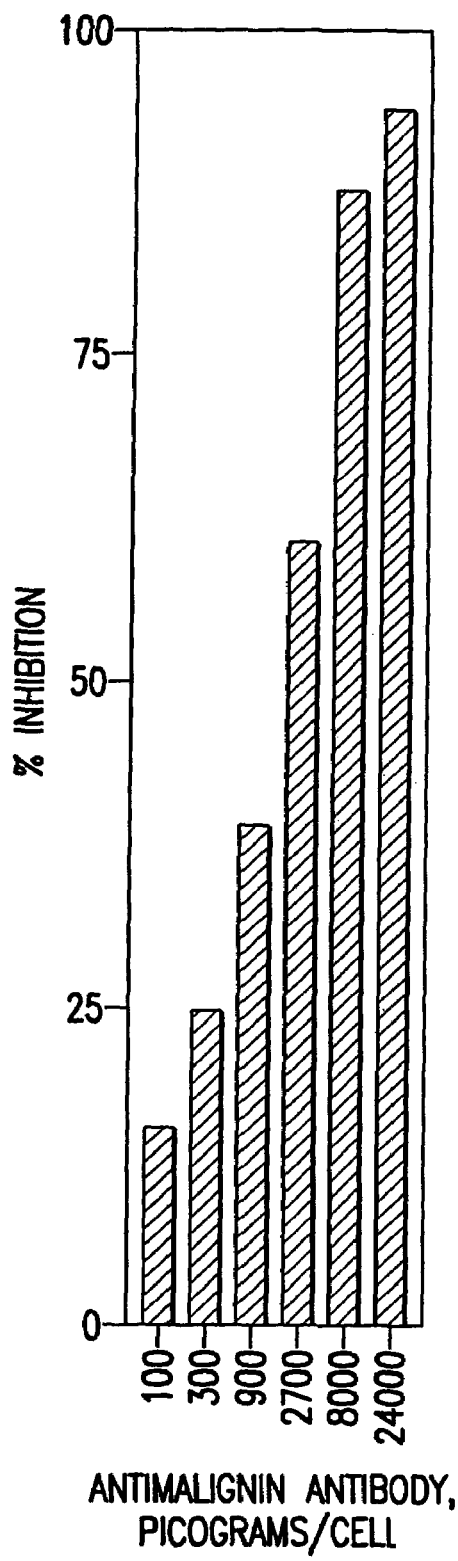
FIG. 6 is a bar graph showing the inhibition of growth of small cell lung carcinoma cells in vitro by anti-malignin antibody.

In addition to the production of novel synthetic products, the fact that these synthetic peptides when injected into an animal induce the production of elevated concentrations of antimalignin antibody establishes that the native biological aglyco substances are in fact responsible for the immune response discovered in human cancer (see FIG. 6).

As previously determined in a 1988 study (*Cancer Detection and Prevention* 12:313-320, 1988), the antimalignin antibody to aglyco 10B is of the IgM type, with little or none being of the IgG type. In the present study where a wholly synthetic antigen, the 12 MER synthetic peptide, was injected into rabbits, a separate determination was made of the antibody produced to determine whether IgG was more prevalent. Thus, the anti-peptide antibody titer also was determined with an enzyme linked immunosorbent assay (ELISA) with free synthetic 16 MER peptide bound in solid phase (1 µg/ml). Results were expressed as the reciprocal of the serum dilution that results in an OD405 of 0.2. Detection was obtained using biotinylated anti-rabbit IgG, HRP-SA conjugate and ABTS. In both rabbits, #507 and #508, the post-injection levels of IgG did not differ from the pre-injection level—all were less than 50. However, see the results below for the 16 MER synthetic peptide.

b) 16 MER Synthetic Peptide

Similarly, on day 1, after the baseline concentration of antimalignin antibody was determined in the serum of two previously uninjected New Zealand white rabbits, #505 and #506, range 3 to 9 months in age, 100 micrograms of the 16 mer synthetic peptide YKAGVAFLHKKNDIDE, synthesized in vitro as described below, conjugated with adjuvant KLH (Keyhole Limpid Hemocyanin) and Freund's adjuvant, were injected subcutaneously in each rabbit. Booster injections of the same peptide were made at day 14 and at day 42. The animals were bled from the auricular artery to determine antimalignin antibody concentration by the standard method as employed in FIG. 6. That is, the antibody was immunoadsorbed against intact immobilized aglyco 10B (malignin) isolated from malignant glioblastoma cells grown in tissue culture. The antibody determinations on rabbit serum were performed at day 21, day 26 and day 55. Both (2/2) rabbits produced additional antimalignin antibody.

Figure 8A:
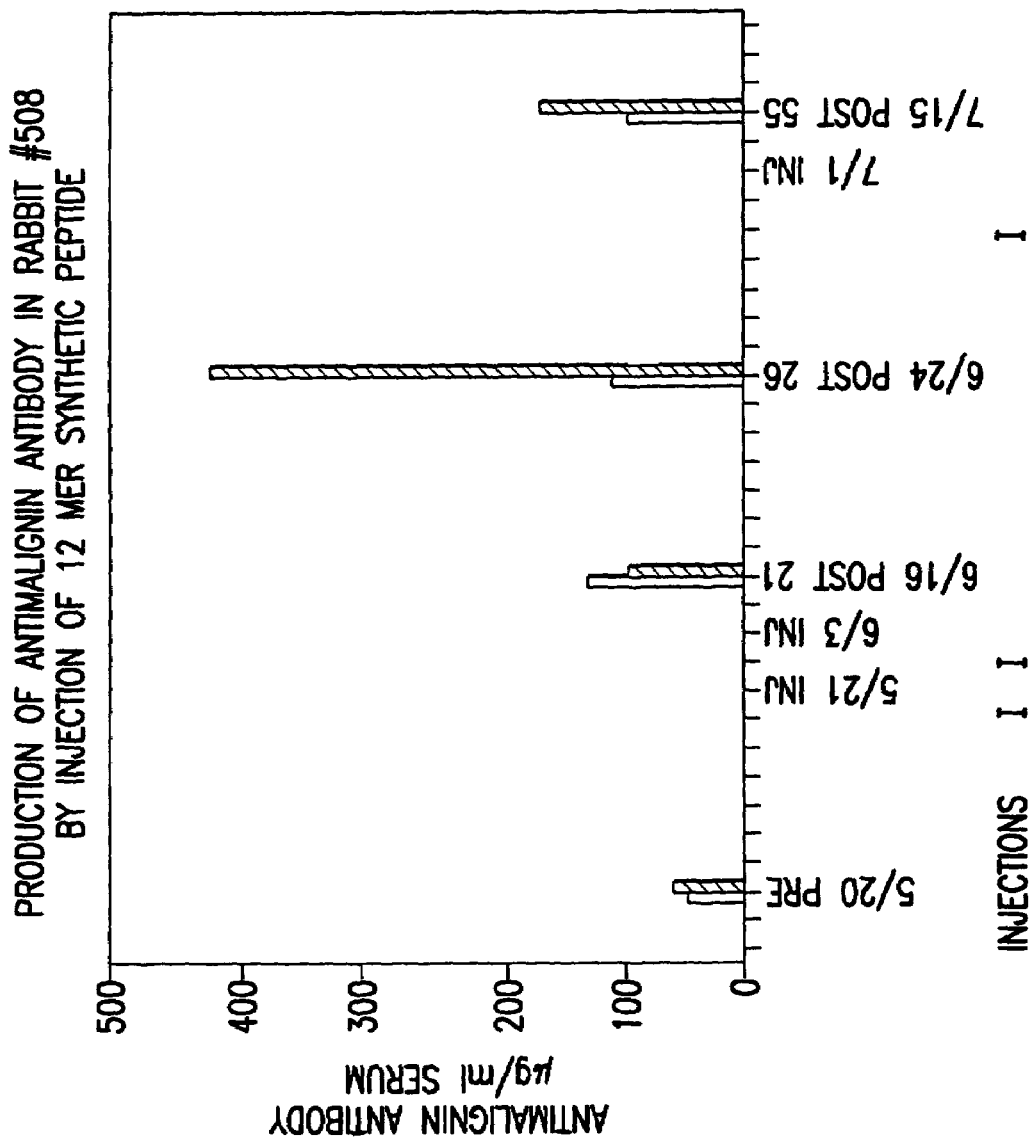
FIGS. 8A and 8B are bar graphs of the amount of anti-malignin antibody produced in vivo upon injection of rabbits with 12-mer synthetic peptide.

For the 16 MER synthetic peptide, FIG. 8A shows the concentrations of antimalignin antibody at each bleed for rabbit #505, both the fast-binding antibody (F-TAG, open columns) and slow-binding antibody (S-TAG, solid columns). S-TAG concentration is seen to increase, but not as much as in FIG. 7A or 7B for the 12 MER synthetic peptide.

Figure 8B:
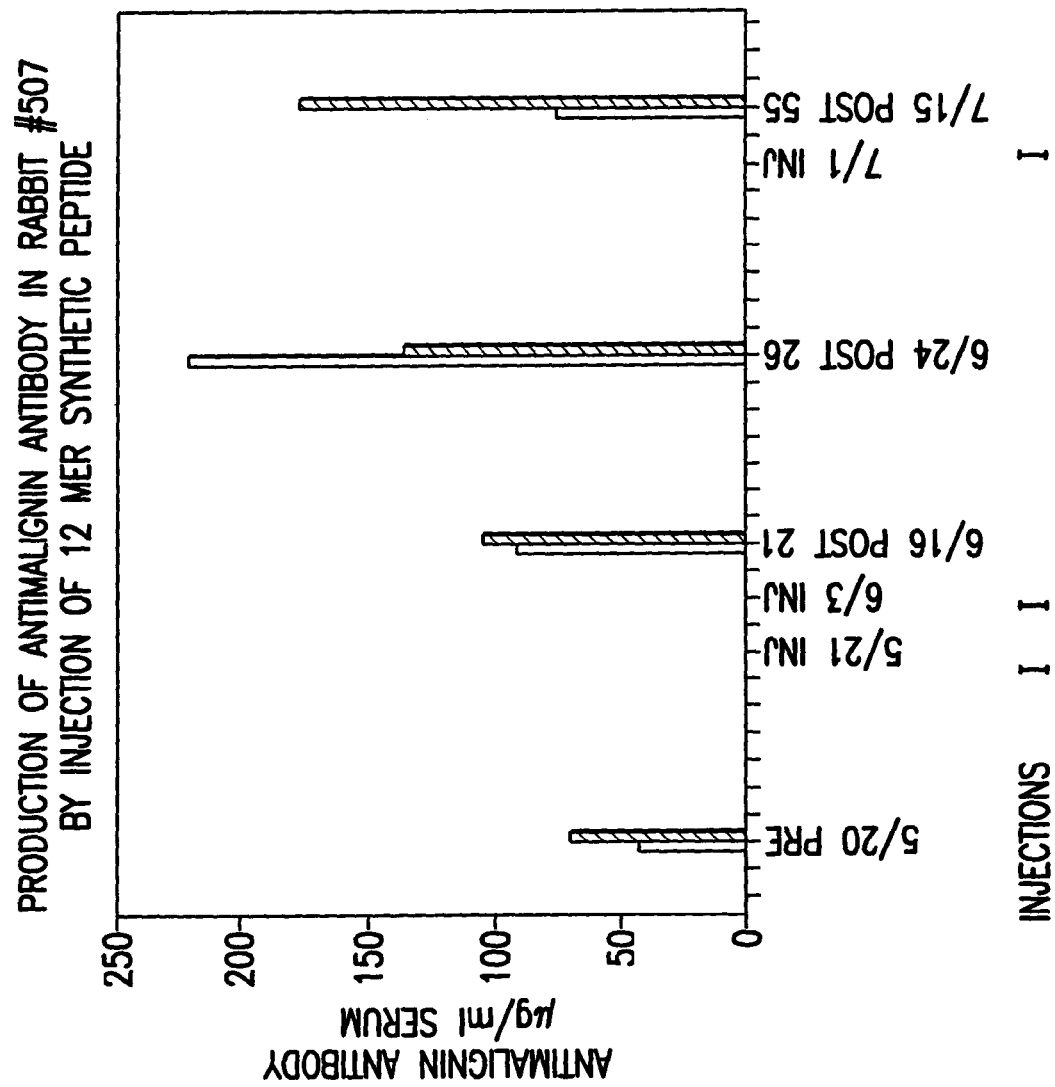
Figure 9A:
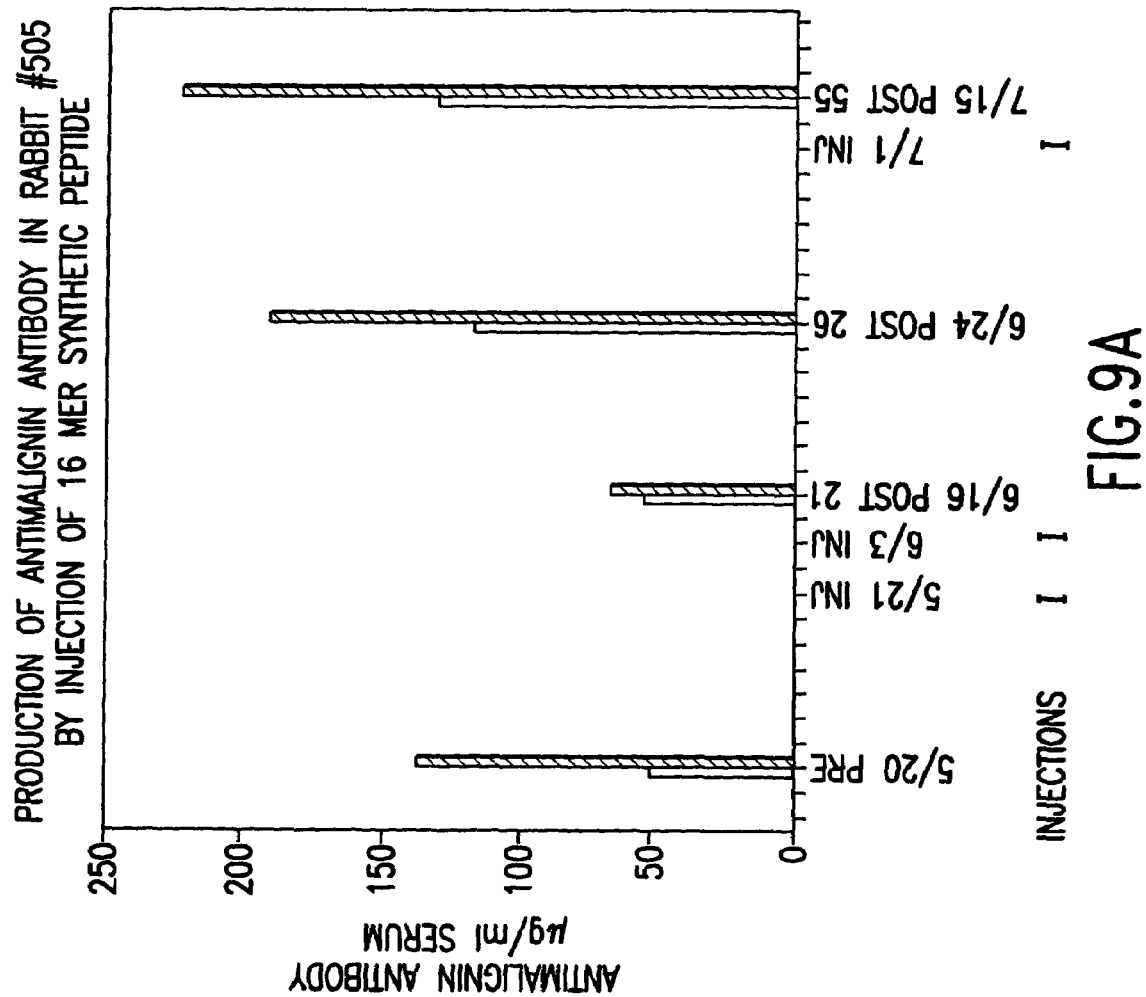

FIG. 8B shows the concentrations of antimalignin antibody at each bleed for rabbit #506, both the fast-binding antibody (F-TAG, open columns) and slow-binding antibody (S-TAG, solid columns). S-TAG concentration is seen to increase approximately 2.5 fold.

Similarly, In vitro, isolated lymphocytes in tissue culture are induced by either the 12 MER synthetic peptide or the 16 MER synthetic peptide, in 1 to 10 microgram amounts per ml, to reproduce antimalignin antibody. In this production, other than the stimulating peptide which is here the synthetic 12 MER or 16 MER peptide rather than the intact Aglyco 10B, the methods used by us are as in Cancer Detection and Prevention 12:313-320, 1988.

As previously determined in the 1988 study, the antimalignin antibody produced both in vivo and in vitro when the 'biological' intact aglyco 10B was the antigen was of the IgM type, with little or none being of IgG type. In the present study where a wholly synthetic antigen, the 16 MER synthetic peptide was injected into rabbits, a separate determination of the antibody produced was made to determine whether IgG was present. Thus, the anti-peptide antibody titer also was determined with an enzyme linked immunosorbent assay (ELISA) with free synthetic 16 MER peptide bound in solid phase (1 µg/ml). Results were expressed as the reciprocal of the serum dilution that results in an OD405 of 0.2. Detection was obtained using biotinylated anti-rabbit IgG, HRP-SA conjugate and ABTS. In contrast to the results obtained with the 12 MER synthetic peptide, for the 16 MER synthetic peptide, in both rabbits #507 and #508, the post-injection levels of IgG rose to a very high level. In both rabbits #507 and #508, the pre-injection level was less than 50; the 26 day level was 18,031 for #507 and 71,326 for #508; the 55 day level was greater than 204,800 in both rabbits #507 and #508. Thus, as well as the products of the IgM form, the IgG type of antimalignin antibody has been produced by injection of the 16 MER synthetic peptide.

Since the previous injection of the 'biological' intact aglyco 10B both into animals and into tissue culture of lymphocytes has always produced antimalignin antibody of the IgM type, and the isolation of the human antibody from human serum also is of the IgM type, it has been assumed that this antibody is not converted to the IgG type as is the case for most but not all antibodies. Thus, the IgG type of antimalignin antibody, produced by injection of the 16 MER synthetic peptide, is a novel antibody. The IgG form has advantages over the IgM type because the IgG type is much smaller in size (150,000 vs. 900,000 Daltons) and therefore will enter both extracellular and intracellular spaces much more easily than the IgM type. This is relevant both to scanning and therapeutic used of the antibody, alone or as carrier for chemotherapeutic agents.

Example 7

Confirmation of the Range of Normal and Elevated Concentrations of Antimalignin Antibody Elevated Antibody Relates Only to Malignant Transformation In studies continuing and expanding those described above, 9,873 individuals including healthy controls, medical disorders, breast and other common cancers regardless of the cell type, transformation to the malignant state has been shown to be associated within days with an increase (above 134 µg/ml) in the concentration of a specific antibody—antimalignin antibody in serum (AMAS) determined by immunoabsorption against the immobilized aglyco-10B antigen (normal levels 0 to 134 micrograms per ml serum). These levels have been confirmed in the present study. As FIG. 10 shows, the increase in concentration of antimalignin antibody does not occur with inflammatory states absent transformation to the malignant state; nor does it occur in purely proliferative states absent transformation, as in benign tumors. FIG. 6 shows that the increase in concentration above normal levels occurs only with transformation to the malignant state, as in FIG. 6 (primary) liver cancer and other cancer, in early active clinical cancer which, is not advanced or terminal. This immune response occurs due to a loss of carbohydrate units in the cancer cell membrane glycoprotein 10B, the consequent exposure of underlying peptide epitopes, the recognition of these epitopes as foreign, and the subsequent production of antimalignin antibody. Results for normal individuals are included in FIG. 6 as controls for the hepatitis/cirrhosis results.

FIG. 6 shows anti-aglyco-10B antibody (anti-malignin antibody) concentration determined in US and Asian individuals. In contrast to a 'false positive' (elevated) rate of 4.5% of U.S. and 8% of Asian healthy controls, antimalignin antibody was found to be increased in concentration above 134 µg/ml in 35.5% of patients with hepatitis/cirrhosis B or C, and in 75% of patients with frankly clinical cancer (some of which may be terminal, thus antibody decreased) following chronic Hepatitis B or C infection, and 95% of other cancers. Since all individuals of the control groups were interspersed at random with the hepatitis cases and determined blind, the differences between the control groups and the hepatitis cases are highly significant ($p<0.001$). Since this antibody is not increased in concentration in many other virus disorders, in other inflammatory, other infectious or medical disorders, no in otherwise healthy controls not associated with hepatitis, cirrhosis or malignancy, it is concluded that, as with other cancers, the increase in antimalignin antibody observed herein signifies the presence of malignant cells. The determination of the concentration of antimalignin antibody in Hepatitis B or C-positive individuals therefore (1) permits detection of the early stages of viral carcinogenesis in human, and (2) can permit the earlier detection and, therefore, treatment of earlier stages than previously possible of malignant transformation in Hepatitis B or C infection.

Furthermore, the sequence of epitopes of malignancy have been determined by hydrolysis and mass spectroscopy, and synthesized. These synthetic peptides are useful as a vaccine to augment the immune response specific to cancer cells. These peptides have been shown to increase the concentration of antimalignin antibody which is cytotoxic at picograms (femtomoles) per cancer cell when injected subcutaneously. (FIG. 5).

Similarly in patients with AIDS, elevation above 134 µg/ml serum in concentration of this antibody, aglyco 10B (antimalignin) antibody, has been observed long before the appearance of clinical cancer in these patients. It is, therefore, concluded that this early transformation to malignancy indicates that immortalization of the cells has occurred, which thereby become safe havens HIV virus. Therefore, these safe havens can be treated just like those in Hepatitis B or C are treated.

Example 8

Automated Methods for the Quantitative Determination of the 12 MER and 16 MER Peptides in Blood and Other Body Fluids in Large Populations No methods have been described previously for the routine quantitative determination of the 12 MER and 16 MER peptide epitopes, nor in fact of the entire Aglyco 10B antigen in the blood or other body fluids, suitable for diagnostic use, nor a method suitable for use by large populations. The methods currently available for determination of the antigens in blood, e.g., use of the tumor markers CEA, PSA and CA125 are not very reliable and have been limited in practical use because they give large false negative and false positive results. For example, the false positive rate of PSA, the prostate specific product release into serum ranges from 15% to 70%, reflecting benign prostatic hypertrophy or exercise rather than cancer of the prostate. Thousands of laboratories make the determination with little inter-laboratory quality control, so that results between laboratories are not comparable. Therefore, new more reliable methods need to be devised which would be suitable for less expensive, practical use by large populations. Furthermore, because the use of the determination of the concentration of antimalignin antibody in serum is not effective as an aid to diagnosis of cancer in advanced or terminal cancer because of the failure at that time of the immune response of antibody, a method for the determination of antigen released into the blood, known to occur more often late in the disease, would be useful but until the present invention none has been available.

The methods which follow are useful for the determination of the 12 MER and 16 MER peptides (antigen) of aglyco 10B, but can be applied to the use of any of the known tumor markers or any other detectable product in the blood or other extracellular fluids. Useful for this procedure is a kit containing (1) a sterilized, bar-coded, graduated, plastic collecting pipette with an expanded head consisting of a compressible bulb ("bulb") and a graduated transparent tapering stem ("stem") approximately 0.1 to 0.3 mm diameter, and approximately 3 to 10 cm long, such as for example, a Transfer Pipette, manufactured by Corning Samco. The pipette stem's inner walls are coated with antimalignin antibody, protease inhibitors and anticoagulant agents; (2) a sterilized lance for pricking the finger to produce a drop of blood; and (3) a requisition form. The drop for blood is drawn into the tip of the pipette and the kit is mailed to the designated laboratory. The collection and shipping kit is preferably small enough to fit into an approximately 4×9-10 inch bar-coded business envelope.

Production of Collecting Pipette Coated with Antibody, Protease Inhibitors and Anticoagulant The pipette is coated with antimalignin antibody, preferably by drawing up the full length of the pipette stem by means of the compressible bulb at the head end of the pipette, from a reservoir of a solution containing antimalignin antibody (Antibody Reservoir), approximately 200 micrograms per ml, plus protease inhibitors (for example, one tablet of Boehringer Mannheim "Complete" Protease Inhibitor per 50 ml which also contains EDTA anticoagulant) allowing the solution to remain in the pipette preferably overnight so that the antibody can adsorb to the walls of the pipette. The solution is then discharged. This production procedure can be automated by an apparatus ("automated pipette loader-discharger") in which a series of pipettes are held in place by squeeze clamps holding the top of each pipette stem in place vertically, the apparatus also contains two flat horizontal metal bars, approximately ¼ inch thick and 1 inch wide, between which the heads of the pipettes are lined up. By moving the two horizontal metal bars together, the compressible bulbs at the head end of the pipettes are squeezed and the contents of the pipettes are discharged. By moving the two horizontal metal bars apart, the compressible bulbs at the head end of the pipettes are relaxed and the reservoir fluid is drawn up into the stem of the pipette from the tip of the pipette which are immersed in the reservoir fluid. After discharging the solution back into the reservoir, the inner walls of the pipette are air-dried by repeatedly automatically squeezing and releasing the compressible bulb in the absence of a reservoir, so that air is drawn in and blown out from the tip of the pipette until the pipette is dry. The concentration of the reservoir fluid is determined after filling a series of pipettes; if the concentration of antibody in the reservoir is less than 100 micrograms per ml, it is reconstituted to approximately 200 micrograms per ml by the addition of the antibody and the protease inhibitors to the reservoir solution. The entire pipette loader-discharger can be tilted approximately 45 degrees so that one position places the pipette tips into one reservoir, and the other position places the pipette tips into another reservoir or a waste discharge vessel or the air.

Obtaining and Shipping the Specimen for Determination in the Laboratory

In the case of blood specimens, the kit preferably contains at least one coated pipette, lance and requisition form which in turn contains instructions for drawing and shipping the blood to the laboratory, as well as the name and address of the physician to whom the results of the determination are to be sent by the laboratory. The individual may fill out the requisition form and place it in the mailer. Hands are carefully washed and the tip of a finger is lanced, then by compressing the head end bulb of the pipette blood is drawn into the tip of the stem of the pipette. The specimen is then mailed to the laboratory.

In the case of specimens of body fluids other than blood, particular instructions may be included in the kit.

Quantitative Determination of the 12 MER and 16 MER Peptides in the Laboratory

When a kit is received by the laboratory, the following general procedure is followed, although the skilled practitioner can make modifications as necessary: (1) the laboratory technician clamps each pipette in series with other pipettes in the automated pipette loader-discharger; (2) the bar code number on each pipette is recorded automatically by a bar code reader and entered into the computer operating the automated pipette loader-discharger (and the results of the determination are listed under this number); (3) the blood volume in each pipette and all of the data on the Requisition Form is recorded by the technician under the bar code number in the computer;(4) the blood is discharged to waste (Reservoir A) from the automated pipette loader-discharger; (5) the inner walls of the pipettes are washed twice with phosphate-buffered saline (PBS) drawn from another reservoir (Reservoir B) automatically by an automated pipette loader-discharger, and each wash fluid is automatically discharged to waste (Reservoir A) by the loader-discharger tilting 45 degrees alternatively so that the vessel for waste discharge is accessed by the pipette tips alternately with the reservoir containing the phosphate-buffered saline; (6) antimalignin antibody is drawn into pipettes from another reservoir (Reservoir C), allowed to remain in contact with the pipette walls for two hours, then discharged to waste (Reservoir A); 7) The pipettes are again washed twice with PBS as in step (5) above; (8) a luminescence emitter such as acridinium ester, bound to anti-human antibody, for example, goat or rabbit anti-human antibody, approximately 100 micrograms per ml, is drawn into pipettes and allowed to remain in contact with the walls of the pipettes for 30 minutes; (9) the pipettes, are washed twice with phosphate-buffered saline (PBS) according to step (5) above; (10) the luminescence emitted is measured by a luminometer, which is swung into place so that its port for receiving the luminescence is directed up against the stem of the pipette, and (11) the luminescence results for each pipette, in luminescent units, are converted by calculation to micrograms. of peptide from a standard curve based on known amounts of an equimolar mixture of the 12 MER and the 16 MER peptides determined by the same procedure, the results are corrected for the volume of original blood in each pipette, and are printed and/or transmitted to any electronic data storage file.

Home Kit

Alternatively, especially for daily monitoring of the concentration of antibodies to the 12 MER and 16 MER peptides in blood or other body fluids (henceforth 'blood'), instead of mailing the blood to the laboratory, the individual or a capable associate at home is provided with equipment and instructions for making the determination at home, the luminometer readings not being observable by the individual, but automatically transmitted via the Internet or other electronic device to the laboratory or the physician. Thus, the individual enters electronically the information on the Requisition Form, reads and enters electronically the volume of blood in the pipette, places the pitpette loaded with blood in the refrigerator (zero to five degrees centigrade)(not frozen) for about two hours, removes the pipette, discharges the blood to a zip-lock sealed waste disposal plastic container which is mailed to the laboratory, washes the pipette twice with phosphate-buffered saline (PBS) provided, the PBS being discharged to the waste disposal container, a luminescence emitter such as but not limited to acridinium ester, bound to anti-human antibody, for example goat or rabbit anti-human antibody, approximately 100 micrograms per ml. is drawn into the pipettes and allowed to remain in contact with the walls of the pipettes for 30 minutes. The pipette contents are discharged to the waste container and the pipette is washed twice with PBS, which is also discharged to the waste container. The pipette is inserted into a luminometer which measures the luminescence emitted. The results for each pipette, in luminescent units, are automatically transmitted via the Internet or other electronic device to the laboratory or physician, converted by calculation to micrograms of antimalignin antibody protein from a standard curve based on known amounts of antimalignin antibody determined by the sample procedure, the results are corrected for the volume of original blood in the pipette, and are printed and/or transmitted to any electronic data storage file.

Example 9

Automated Method for the Quantitative Determination of the Specific Antibodies to the 12 MER and 16 MER Peptides in Blood and Other Body Fluids in Large Populations The method now available for determination of the antibody to these two peptides (antimalignin antibody), although carefully worked out, quantitative, and reliable, are markedly limited in practical use because they require special tubes for drawing and shipping, a laboratory, phlebotomist or physician to draw the blood specimen from veins, a procedure for clotting of blood, centrifugation in a refrigerated centrifuge, immediate shipment overnight on dry ice—all of which are time-consuming or not readily available in most areas and expensive. In addition, present methods for the production of the reagent, covalently bound maligning biologically produced from malignant glioblastoma cells grown in tissue culture, extracted, isolated, purified and covalently bound to bromo acetyl cellulose—and immediate determination in an expensive, manual, non-automated 6-hour immunoabsorption methods which requires much personal training and a high level of compulsive care in performance against standards. Therefore, new methods are necessary which are suitable for less expensive practical use by large populations.

Most of the above precautions for drawing, shipping and prompt determination of the antibody were undertaken to avoid loss or reproducibility found to be due to storing serum in antibody absorbing tubes or storing beyond 8 hours at temperatures less than −70° C. (*Cancer Detection and Prevention* 11:100, 1987). It has now been discovered that these expensive and time-consuming precautions, not universally available, are obviated if the whole blood is collected and shipped in a container with anticoagulant and protease inhibitors and either the peptides or the antibody determined automatically by the antibody of the peptide respectively, bound to a luminescence-emitting substrate. The present invention now makes available an affordable test for an antimalignin antibody, for use in large populations.

The methods which follow are for the determination generally of the antibody to the 12 MER and 16 MER synthetic peptides (antigen) but can be applied to the determination of any other antibodies in the blood or other extracellular fluids.

The following kit is useful for carrying out this procedure. A kit containing (1) a sterilized, bar-coded, graduated, plastic collecting pipette with an expanded head consisting of a compressible bulb ("bulb") and a graduated transparent tapering stem ("stem") approximately 0.1 to 0.3 mm diameter, and approximately 3 to 10 cm long, such as, for example, a Transfer Pipette, for example, as manufactured by Corning Samco. The pipette stem's inner walls are coated with an equimolar mixture of the 12 MER and the 16 MER synthetic peptides, protease inhibitors and anticoagulant agents; (2) a sterilized lance for pricking the finger to produce a drop of blood; and (3) a requisition form. The drop of blood is drawn into the tip of the pipette and the kit is mailed to the designated laboratory. The collection and shipping kit is small enough to fit into an approximately 4×9-10 inch bar-coded business envelope.

Production of Collecting Pipette Coated with the 12 MER and the 16 MER Synthetic Peptides, Protease Inhibitors and Anticoagulant The pipette is coated with an equimolar mixture of the 12 MER and the 16 MER synthetic peptides ("peptides"), preferably by drawing up the full length of the pipette stem with the compressible bulb at the head end of the pipette from a reservoir ("Peptide Reservoir") of a solution containing one of, or an equimolar mixture of, the 12 MER and the 16 MER synthetic peptides, approximately 200 micrograms per ml, plus protease inhibitors (for example, one tablet of Boehringer Mannheim "Complete" Protease Inhibitor per 50 ml which also contains EDTA anticoagulant) allowing the solution to remain in the pipette, preferably overnight, so that the peptides can adsorb to the walls of the pipette. The solution is then discharged. This production procedure can be automated by an apparatus ("automated pipette loader-discharger") in which a series of pipettes are held in place by squeeze clamps holding the top of each pipette stem in place vertically, the apparatus also containing two flat horizontal metal bars, approximately ¼ inch thick and 1 inch wide, between which the heads of the pipettes are lined up. By moving the two horizontal metal bars together, the compressible bulbs at the head end of the pipettes are squeezed and the contents of the pipettes are discharged. By moving the two horizontal metal bars apart, the compressible bulbs at the head end of the pipettes are relaxed and the reservoir fluid is drawn up into the stem of the pipette from the tip of the pipettes which are immersed in the reservoir fluid. After discharging the solution back into the reservoir, the inner walls of the pipette are air-dried by repeatedly automatically squeezing and releasing the compressible bulb in the absence of a reservoir, so that air is drawn in and blown out from the tip of the pipette until the pipette is dry. The concentration of the Peptide Reservoir fluid is determined after filling a series of pipettes; if the concentration of peptide(s) in the reservoir is less than 100 micrograms per ml, it is reconstituted to approximately 200 micrograms per ml by the addition of the antibody and the protease inhibitors to the reservoir solution. The entire pipette loader-discharger can be tilted approximately 45 degrees so that one position places the pipette tips into one reservoir, and the other position places the pipette tips into another reservoir or a waste discharge vessel or the air.

Obtaining and Shipping the Specimen for Determination in the Laboratory

In the case of blood specimens, the kit preferably contains at least one coated pipette, lance and requisition form which in turn contains instructions for drawing and shipping the blood to the laboratory, as well as the name and address of the physician to whom the results of the determination are to be sent by the laboratory. The individual may fill out the requisition form and place it in the mailer. Hands are carefully washed and the tip of a finger is lanced. Then, by compressing the head end bulb of the pipette, the blood is drawn into the tip and up the stem of the pipette. The specimen is then mailed to the laboratory.

In the case of specimens of body fluids other than blood, particular instructions may be included in the kit.

Quantitative Determination of the Antibodies to the Aglyco 10B 12 MER and 16 MER Peptides in the Laboratory When the kit is received by the laboratory, (1) the laboratory technician clamps each pipette in series with other pipettes in the automated pipetted loader-discharger; (2) the bar code number on each pipette and all the data on the Requisition Form is recorded automatically by a bar code reader and entered into the computer operating the automated pipette loader-discharger (and the results of the determination are listed under this number; (3) the blood volume in each pipette is recorded by the technician under the bar code number in the computer;(4) the blood is discharged to waste (Reservoir A) from the automated pipette loader-discharger; (5) the inner walls of the pipettes are washed twice with phosphate-buffered saline (PBS) drawn from another reservoir (Reservoir B) automatically by an automated pipette loader-discharger, and each wash fluid is automatically discharged to waste (Reservoir A) by the loader-discharger tilting 45 degrees alternatively so that the vessel for waste discharge is accessed by the pipette tips alternately with the reservoir containing the phosphate-buffered saline; (6) antimalignin antibody is drawn into pipettes from another reservoir (Reservoir C), allowed to remain in contact with the pipette walls for two hours, then discharged to waste (Reservoir A); 7) the pipettes are again washed twice with PBS as in step (5) above; (8) a luminescence emitter such as acridinium ester, bound to anti-human antibody, for example, goat or rabbit anti-human antibody, approximately 100 micrograms per ml, is drawn into pipettes and allowed to remain in contact with the walls of the pipettes for 30 minutes; (9) the pipettes, are washed twice with phosphate-buffered saline (PBS) according to step (5) above; (10) the luminescence emitted is measured by a luminometer, which is swung into place so that its port for receiving the luminescence is directed up against the stem of the pipette, and (11) the luminescence results for each pipette, in luminescent units, are converted by calculation to micrograms of antibody from a standard curve based on known amounts of antimalignin antibody determined by the same procedure, the results are corrected for the volume of original blood in each pipette, and are printed and/or transmitted to any electronic data storage file.

Home Kit

Alternatively, especially for daily monitoring of the concentration of antibodies to the 12 MER and 16 MER peptides in blood or other body fluids (henceforth 'blood'), instead of mailing the blood to the laboratory, the individual or a capable associate at home is provided with equipment and instructions for making the determination at home, the luminometer readings not being observable by the individual, but automatically transmitted via the Internet or other electronic device to the laboratory or the physician. Thus, the individual enters electronically the information on the Requisition Form, reads and enters electronically the volume of blood in the pipette, places the pitpette loaded with blood in the refrigerator (zero to five degrees centigrade)(not frozen) for about two hours, removes the pipette, discharges the blood to a zip-lock sealed waste disposal plastic container which is mailed to the laboratory, washes the pipette twice with phosphate-buffered saline (PBS) provided, the PBS being discharged to the waste disposal container, a luminescence emitter such as but not limited to acridinium ester, bound to anti-human antibody, for example goat or rabbit anti-human antibody, approximately 100 micrograms per ml. is drawn into the pipettes and allowed to remain in contact with the walls of the pipettes for 30 minutes. The pipette contents are discharged to the waste container and the pipette is washed twice with PBS, which is also discharged to the waste container. The pipette is inserted into a luminometer which measures the luminescence emitted. The results for each pipette, in luminescent units, are automatically transmitted via the Internet or other electronic device to the laboratory or physician, converted by calculation to micrograms of antimalignin antibody protein. from a standard curve based on known amounts of antimalignin antibody determined by the sample procedure, the results are corrected for the volume of original blood in the pipette, and are printed and/or transmitted to any electronic data storage file.

Example 10B

Structure of Aglyco 10B

A. Iodobenzoic Acid Hydrolysis of Aglyco 10B followed by Edman Degradation yielded the peptide ("Iodopeptide") with the following sequence:

| Y | K | A | G | V | A | F | L | H | K | K | N | D | I | D | E |
|---|---|---|---|---|---|---|---|---|---|---|---|---|---|---|---|
| Amino Acid Residue Numbers: 1 | 2 | 3 | 4 | 5 | 6 | 7 | 8 | 9 | 10 | 11 | 12 | 13 | 14 | 15 | 16 |

B. Mass spectrometry followed by calculations using MacBioSpec Software Manual 013048-A, PESCIEX, Perkin Elmer Sciex Instruments, yielded the following properties of the peptide YKAGVAFLHKKNDIDE:

| | |
|---|---|
| N- Terminal Group: Hydrogen | C- Terminal Group: Free Acid |
| MH+ Monoisotopic Mass = 1847.9656 amu | HPLC index = 43.40 |
| MH+ Average Mass = 1849.0998 amu | Bull & Breese value = −80 |
| Isoelectric Point (pI) = 8.0 | Elemental Composition: $C_{84}H_{131}N_{22}O_{25}$ |

C. Mass spectrometry: The sequence of "iodopeptide" in 1A above obtained by Iodobenzoic acid hydrolysis was independently confirmed by mass spectrometry of fragments of Aglyco 10B obtained by four different acid hydrolyses of Aglyco 10B in solution and of Aglyco 10B immobilized on bromoacetyl-cellulose (Aglyco 10BC; or A10BC) as below. These hydrolyses produced 13 overlapping hydrolytic fragments (two of which, 6-10 and 6-12 below, were obtained by two different hydrolytic methods). Taken together, these overlapping fragments independently confirmed the peptide sequence of "Iodopeptide" YKAGVAFLHKKNDIDE as follows.

| FRAGMENT IDENTIFIED | | | METHOD BY WHICH FRAGMENT OBTAINED | | | |
|---|---|---|---|---|---|---|
| (amino acid residue numbers) | MH+ (mass) | SEQUENCE* | Aglyco 10B Auto-hydrolysis** | A10BC Auto-hydrolysis | A10BC Microwaved 5 seconds | A10BC Microwaved 30 seconds |
| 1-3 | 381.21 | ( )YKA(G) | | | | + |
| 1-5 | 537.30 | ( )YKAGV(A) | | + | | |
| 2-6 | 445.28 | (Y)KAGVA(F) | | + | | |
| 2-7 | 592.35 | (Y)KAGVAF(L) | | | + | |
| 4-11 | 899.55 | (A)GVAFLHKK(N) | | | | + |
| 5-7 | 336.19 | (G)VAF(L) | | | | + |
| 6-7 | 237.12 | (V)AF(L) | + | | | |
| 6-10 | 615.36 | (V)AFLHK(K) | | | | + |
| 6-10 | 615.36 | (V)AFLHK(K) | + | | | |
| 6-12 | 857.50 | (V)AFLHKKN(D) | | + | | |
| 6-12 | 857.50 | (V)AFLHKKN(D) | + | | | |
| 7-8 | 279.17 | (A)FL(H) | | | + | |
| 10-16 | 861.43 | (H)KKNDIDE( ) | + | | | |
| 11-14 | 489.27 | (K)KNDI(D) | + | | | |
| 12-15 | 476.20 | (K)NDID(E) | + | | | |

*Standard Letter Code for amino acid is as follows:
Y = Tyrosine;
K = Lysine;
A = Alanine;
G = Glycine;
V = Valine;
F = Phenylalanine;
L = Leucine;
H = Histidine;
N = Asparagine;
D = Aspartic Acid;
I = Isoleucine;
E = Glutamic Acid.
( ) = the amino acid linked to the N-and the C-terminal amino acid of the fragment.
**Intact Aglyco 10B in solution is a strong acid, with an isoelectric point of approximately 2.7, and produces autohydrolysis when left at room temperature for hours, or even at 0-5° C. for longer periods.

C. Trypsin hydrolysis of Aglyco 10B followed by Edman Degradation yielded the peptide ("Trypsinpeptide") with the following sequence:

|   | G | L | S | D | G | S | N | T | E | S | D | I |
|---|---|---|---|---|---|---|---|---|---|---|---|---|
| Amino Acid Residue Numbers: | 1 | 2 | 3 | 4 | 5 | 6 | 7 | 8 | 9 | 10 | 11 | 12 |

D. Mass spectrometry of hydrolytic fragments of Aglyco 10B followed by calculations using MacBioSpec Software Manual 013048-A, PESCIEX, Perkin Elmer Sciex Instruments, yielded the following properties of the "Trypsinpeptide" GLSDGSNTESDI:

N- Terminal Group: Hydrogen   C- Terminal Group: Free Acid
MH+ Monoisotopic Mass = 1194.5126 amu   HPLC index = 0.70
MH+ Average Mass = 1195.1817 amu
Isoelectric Point (pI) = 4.4   Butt & Breese value = 2690
Elemental Composition: $C_{46}H_{76}N_{13}O_{24}$ E. Mass spectrometry: The sequence of amino acids 2-11 of "Trypsinpeptide" in 2C. above obtained by trypsin hydrolysis was independently confirmed by mass spectrometry of fragments of Aglyco 10B obtained by four different acid hydrolyses of Aglyco 10B in solution and of Aglyco 10B immobilized on bromoacetyl-cellulose (Aglyco 10B-cellulose; or A10BC) as below. These hydrolyses produced seven overlapping hydrolytic fragments which independently confirmed 2-11 of the peptide sequence of "Trypsinpeptide" (G)LSDGSNTESD(I) as follows:

| FRAGMENT IDENTIFIED | | | METHOD BY WHICH FRAGMENT OBTAINED | | | |
|---|---|---|---|---|---|---|
| (amino acid residue numbers) | MH+ (mass) | SEQUENCE* | Aglyco 10B Auto-hydrolysis** | A10BC Auto-hydrolysis | A10BC Microwaved 5 seconds | A10BC Microwaved 30 seconds |
| 2-7 | 592.26 | (G) LSDGSN (T) | | | | + |
| 3-5 | 278.10 | (L) SDG (S) | | | | + |
| 4-6 | 278.10 | (S) DGS (N) | | | | + |
| 4-11 | 824.29 | (S) DGSNTESD (I) | | | + | |

| FRAGMENT IDENTIFIED | | | METHOD BY WHICH FRAGMENT OBTAINED | | | |
|---|---|---|---|---|---|---|
| (amino acid residue numbers) | MH+ (mass) | SEQUENCE* | Aglyco 10B Auto-hydrolysis** | A10BC Auto-hydrolysis | A10BC Microwaved 5 seconds | A10BC Microwaved 30 seconds |
| 5-8 | 378.16 | (D) GSNT (E) | + | | | |
| 6-10 | 537.22 | (G) SNTES (D) | | | + | |
| 8-10 | 336.14 | (N) TES (D) | | | | + |

*Standard Letter Code for amino acid is as follows:
G = Glycine;
L - Leucine;
S = Serine;
D = Aspartic Acid;
N = Asparagine;
T = Threonine;
E = Glutamic Acid;
I = Isoleucine
**Intact Aglyco 10B in solution is a strong acid, with an isoelectric point of approximately 2.7, and produces autohydrolysis when left at room temperature for hours, or even at 0-5° C. for longer periods of weeks to months.

F. CNBr Hydrolysis of Aglyco 10B followed by Edman degradation yielded the dipeptide ("CNBrpeptide") with the following sequence: M D Amino Acid Residue Numbers: 1 2

G. A chromophore group ("Chromophore") is present in Aglyco 10B which results in Aglyco 10B being slightly yellow in a concentrated solution (>100 μg/ml) and demonstrating an absorption spectra as shown in FIG. 5. The Chromophore remains with Aglyco 10B throughout all phases of its purification including high pressure liquid chromatography.

When oxygen is replaced by nitrogen by evacuating and heat=sealing the glass tube which contains the Aglyco 10B solution, the Aglyco 10B solution turns dark green.

When the glass tube is opened to the air, the solution immediately returns to the yellow color.

Since this transition from yellow to the oxygenated state to dark green in the anoxic state and back to yellow in the oxygenated state is a reversible transition seen only in relation to the presence or absence of oxygen, it is concluded that the color change is the property of reversible oxidation: reduction of the Chromophore.

H. Cloning the gene for Aglyco 10B

By methods well known in the art, the gene for Aglyco 10B and thus for 10B as well, with full amino acid sequence, is derived using either the "Iodopeptide" above or the "Trypsinpeptide" above, or both, to construct RNA and a cDNA probe of normal and transformed glial cell libraries. The gene for Aglyco 10B and of glycoprotein 10B permits their use in their entirety, or with fragments of the structure, as vaccines. In addition, the entire gene or parts thereof can be introduced into various well known expression systems to produce intact 10B glycoconjugated protein or Aglyco 10B, and these products used as vaccines in the patients, or in animals to produce the specific antibodies to the intact molecules or fragments thereof. Since glycoprotein 10B is known to be involved in recognition and cognitive training in the whole animal, it can be administered to improve cognitive function in animals and man.

What is claimed is:

1. A purified monoclonal antibody which specifically recognizes a peptide consisting of the amino acid sequence of SEQ ID NO:2.

2. A composition for increasing the concentration of antibodies to aglycoprotein 10B antigenic epitopes, the composition comprising a peptide selected from the group consisting of the peptide consisting of SEQ ID NO:1, the peptide consisting of SEQ ID NO:2, and combinations thereof.

3. A kit for determining the concentration of aglycoprotein 10B antigenic epitopes present in blood of a patient comprising at least one blood collection tube or pipette and a purified monoclonal antibody that specifically recognizes the peptide consisting of SEQ ID NO:1 or the peptide consisting of SEQ ID NO:2 wherein said antibody is coated on the inner surface of said collection tube or pipette.

4. A kit for determining the concentration of aglycoprotein 10B antigenic epitopes present in blood of a patient comprising at least one blood collection tube or pipette and a peptide consisting of the amino acid sequence of SEQ ID NO:1 or SEQ ID NO:2.

5. The kit of claim 4 wherein the peptide is coated on the inner surface of the tube or pipette.

6. An isolated nucleic acid encoding a peptide consisting of the amino acid sequence of SEQ ID NO:1 or SEQ ID NO:2.

7. The composition of claim 2 further comprising a pharmaceutically acceptable carrier.

* * * * *